United States Patent
Uger et al.

(10) Patent No.: US 10,053,510 B2
(45) Date of Patent: Aug. 21, 2018

(54) FASR ANTIBODIES AND METHODS OF USE

(71) Applicant: ProMIS Neurosciences Inc., Toronto (CA)

(72) Inventors: Marni Diane Uger, Richmond Hill (CA); Veronica Ciolfi, Brampton (CA); Neil R. Cashman, Vancouver (CA)

(73) Assignees: PROMIS NEUROSCIENCES INC., Toronto (CA); THE UNIVERSITY OF BRITISH COLUMBIA, Vancouver (CA)

( * ) Notice: Subject to any disclaimer, the term of this patent is extended or adjusted under 35 U.S.C. 154(b) by 38 days.

(21) Appl. No.: 14/893,847

(22) PCT Filed: May 26, 2014

(86) PCT No.: PCT/CA2014/000457
§ 371 (c)(1),
(2) Date: Nov. 24, 2015

(87) PCT Pub. No.: WO2014/186877
PCT Pub. Date: Nov. 27, 2014

(65) Prior Publication Data
US 2016/0215055 A1 Jul. 28, 2016

Related U.S. Application Data

(60) Provisional application No. 61/827,255, filed on May 24, 2013.

(51) Int. Cl.
| | |
|---|---|
| *C07K 16/28* | (2006.01) |
| *G01N 33/566* | (2006.01) |
| *A61K 47/48* | (2006.01) |
| *G01N 33/68* | (2006.01) |
| *A61K 49/00* | (2006.01) |
| *G01N 33/569* | (2006.01) |
| *A61K 39/00* | (2006.01) |

(52) U.S. Cl.
CPC ...... *C07K 16/2878* (2013.01); *A61K 39/0005* (2013.01); *A61K 47/48561* (2013.01); *A61K 49/001* (2013.01); *C07K 16/2872* (2013.01); *G01N 33/566* (2013.01); *G01N 33/56966* (2013.01); *G01N 33/6893* (2013.01); *A61K 2039/55566* (2013.01); *C07K 2317/21* (2013.01); *C07K 2317/34* (2013.01); *C07K 2317/56* (2013.01); *C07K 2317/565* (2013.01); *G01N 2333/70578* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,399,216 A | 8/1983 | Axel et al. |
| 4,634,665 A | 1/1987 | Axel et al. |
| 5,179,017 A | 1/1993 | Axel et al. |
| 5,476,996 A | 12/1995 | Wilson et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,675,063 A | 10/1997 | Knight |
| 5,698,767 A | 12/1997 | Wilson et al. |
| 5,770,429 A | 6/1998 | Lonberg et al. |
| 5,789,650 A | 8/1998 | Lonberg et al. |
| 5,795,728 A | 8/1998 | Dimri et al. |
| 5,814,318 A | 9/1998 | Lonberg et al. |
| 5,830,469 A | 11/1998 | Bini |
| 5,869,046 A | 2/1999 | Presta et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 6,015,559 A | 1/2000 | Lynch et al. |
| 6,075,181 A | 6/2000 | Kucherlapati et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,162,963 A | 12/2000 | Kucherlapati et al. |

(Continued)

FOREIGN PATENT DOCUMENTS

| | | |
|---|---|---|
| EP | 154316 A2 | 11/1985 |
| EP | 338841 A1 | 4/1989 |

(Continued)

OTHER PUBLICATIONS

GenBank Database, Fas antigen [*Homo sapiens*], Accession No. AAA63174, version AAA63174.1, accessed May 2, 2017, Mar. 6, 1995.*
Newswire, [retrieved online} URL:<http://www.newswire.ca/news-releases/amorfix-announces-the-development-of-antibodies-that-bind-to-misfolded-fas-receptor-protein-as-a-potential-treatment-for-cancer-510245181.html>, [retrieved on May 2, 2017] May 15, 2012.*
Kay, M. M.B., Localization of senescent cell antigen on band 3. PNAS USA, Sep. 1984, vol. 81, pp. 5753-5757.
Pani, G. From growing to secreting: New roles for mTOR in aging cells. Cell Cycle, Aug. 2011, vol. 10, pp. 2450-2453.

(Continued)

*Primary Examiner* — Claire Kaufman
(74) *Attorney, Agent, or Firm* — Bereskin & Parr LLP; Carmela De Luca

(57) ABSTRACT

Provided herein are an exogenous antibody that binds selectively to a misfolded form of human FasR, and methods and uses for said antibody. Specifically disclosed is the antibody designated AMF 3a-118 which selectively binds the peptide represented by LHHDGQFCH (SEQ ID NO:2) and the antibody designated AMF 3d-19 which selectively binds the peptide represented by NSTVCEH (SEQ ID NO:5).

13 Claims, 5 Drawing Sheets

(56) References Cited

U.S. PATENT DOCUMENTS

| | | |
|---|---|---|
| 6,194,551 B1 | 2/2001 | Idusogie et al. |
| 6,846,637 B1 | 1/2005 | Chiodi |
| 7,041,807 B1 | 5/2006 | Cashman et al. |
| 7,186,800 B1 | 3/2007 | Gentz et al. |
| 7,285,267 B2 | 10/2007 | Gentz et al. |
| 7,510,710 B2 | 3/2009 | Newell et al. |
| 7,534,428 B2 | 5/2009 | Gentz et al. |
| 8,158,347 B2 | 4/2012 | Sharpless et al. |
| 2003/0153043 A1 | 8/2003 | Carr et al. |
| 2006/0161995 A1 | 7/2006 | Kuroiwa et al. |
| 2013/0330275 A1 | 12/2013 | Cashman et al. |

FOREIGN PATENT DOCUMENTS

| | | |
|---|---|---|
| EP | 401384 A1 | 12/1990 |
| EP | 1391511 A1 | 2/2004 |
| WO | 8704462 A1 | 1/1987 |
| WO | 8901036 A1 | 7/1987 |
| WO | 9203918 A1 | 3/1992 |
| WO | 9312227 A1 | 6/1993 |
| WO | 9425585 A1 | 11/1994 |
| WO | 94/029351 A2 | 12/1994 |
| WO | 9713852 A1 | 4/1997 |
| WO | 9824884 A1 | 5/1998 |
| WO | 9945962 A1 | 9/1999 |
| WO | 00/42072 A2 | 7/2000 |
| WO | 0114424 A2 | 3/2001 |
| WO | 0243478 A2 | 6/2002 |
| WO | 03/000853 A2 | 1/2003 |
| WO | 2004/113387 A2 | 12/2004 |
| WO | 2008/080623 A2 | 7/2008 |
| WO | 2010/006772 A2 | 1/2010 |
| WO | 2010/040209 A1 | 4/2010 |
| WO | 2010/099612 A1 | 9/2010 |
| WO | 2013/185215 A1 | 12/2013 |
| WO | 2014/186878 A1 | 11/2014 |

OTHER PUBLICATIONS

Golde, T.E. et al. Proteinopathy-induced neuronal senescence: a hypothesis for brain failure in Alzheimer's and other neurodegenerative diseases. Alzheimer's Research & Therapy, Oct. 2009, vol. 1, p. 5.

Decaudin, D. et al. Distinct Experimental Efficacy of Anti-Fas/AP0-1/CD95 Receptor Antibody in Human Tumors. Experimental Cell Research. Aug. 15, 2001. vol. 268, No. 2, pp. 162-168.

Garrett T.P.J. et al. Antibodies specifically targeting a locally misfolded region of tumor associated EGFR. Proceedings of the National Academy of Science of the United States of America. Mar. 31, 2009. vol. 106, No. 13, pp. 5082-5087.

Baker et al. Clearance of p16Ink4a-positive senescent cells delays ageing-associated disorders, Nature, Nov. 2, 2011, vol. 479, No. 7372, pp. 232-236.

Shields et al. High Resolution Mapping of the Binding Site on Human IgG1 for FcgRI, FcgRII, FcgRIII, and FcRn and Design of IgG1 Variants with Improved Binding to the FcgR. J. Biol. Chem. vol. 276, No. 9, Mar. 2, 2001, pp. 6591-6604.

Taylor et al. A transgenic mouse that expresses a diversity of human sequence heavy and light chain immunoglobulins. Nucleic Acids Research, 1992. vol. 20, No. 23, pp. 6287-6295.

Tuaillon et al., Human immunoglobulin heavy-chain minilocus recombination in transgenic mice: Gene-segment use in u and y transcripts. Proc. Natl. Acad. Sci. USA. vol. 90, pp. 3720-3724, Apr. 1993.

Chen et al. B cell development in mice that lack one or both immunoglobulin x light chain genes. The EMBO Journal, 1993, vol. 12, No. 3, pp. 821-830.

Tomizuka et al. Double trans-chromosomic mice: Maintenance of two individual human chromosome fragments containing Ig heavy and k loci and expression of fully human antibodies. Proc. Natl. Acad. Sci. USA, Jan. 18, 2000, vol. 97, No. 2, pp. 722-727.

Takebe et al. SR alpha promoter: an efficient and versatile mammalian cDNA expression system composed of the simian virus 40 early promoter and the R-U5 segment of human T-cell leukemia virus type 1 long terminal repeat. Mol. Cell Biol. Jan. 1988; vol. 8, No. 1, pp. 466-472.

Urlaub and Chasin. Isolation of Chinese hamster cell mutants deficient in dihydrofolate reductase activity. Jul. 1980; vol. 77, No. 7, pp. 4216-4220.

Bueler et al., Mice devoid of PrP are resistant to scrapie. Cell. Jul. 2, 1993. vol. 73, No. 7: 1339-47.

Fischer et al., Prion protein (PrP) with amino-proximal deletions restoring susceptibility of PrP knockout mice to scrapie. The EMBO Journal 1996, vol. 15, No. 6, pp. 1255-1264.

Weissmann and Flechsig, PrP Knock-out and PrP Transgenic Mice in Prion Research. Br Med Bull, 2003; 66: 43-60.

Moynagh and Schimmel, Tests for BSE evaluated. Nature, 400: 105, 1999.

Taylor et al. (1994) Human immunoglobulin transgenes undergo rearrangement, somatic mutation and class switching in mice that lack endogenous IgM. International Immunology 6 : 579-591.

Morrison, S. Transfectomas provide novel chimeric antibodies. (1985) Science 229: 1202.

Scheraga et al., Retention of the Cis Proline Conformation in Tripeptide Fragments of Bovine Pancreatic Ribonuclease A Containing a Non-natural Proline Analogue, 5,5-Dimethylproline. J. Am. Chem. Soc. 1999, 121, 11558-11566.

Wang et al. Serine-cis-proline and serine-trans-proline isosteres: stereoselective synthesis of (Z)- and (E)-alkene mimics by Still-Wittig and Ireland-Claisen rearrangements. J. Org. Chem. (Mar. 2003), vol. 68, No. 6, pp. 2343-2349.

Chandler RL. Encephalopathy in mice produced by inoculation with scrapie brain material. Lancet, Jun. 1961, vol. 1, No. 7191, pp. 1378-1379.

Carlson et al., Linkage of Prion Protein and Scrapie Incubation Time Genes. vol. 46, Issue 4, Aug. 15, 1986, pp. 503-511.

Fischer et al., Binding of disease-associated prion protein to plasminogen. Nature, Nov. 23, 2000, 408(6811): 479-83.

\* cited by examiner

FASR ANTIBODIES AND METHODS OF USE

RELATED APPLICATIONS

This application is a national phase entry of PCT/CA2014/000457, filed May 26, 2014, which claims priority from U.S. Provisional patent application Ser. No. 61/827,255 filed May 24, 2013, each of these applications being incorporated herein in their entirety by reference.

INCORPORATION OF SEQUENCE LISTING

A computer readable form of the Sequence Listing "15289-P46231US01_SL.txt" (38,402 bytes), submitted via EFS-WEB and created on Jan. 25, 2016, is herein incorporated by reference.

FIELD OF THE INVENTION

This invention relates to antibodies that bind selectively to a disease form of the human Fas receptor, FasR, and to uses thereof for medical diagnosis and therapeutic intervention.

BACKGROUND TO THE INVENTION

About one-third of the population of the developed world is destined to die from cancer. Current treatment for cancers—including chemotherapy and radiotherapy—are based on killing cancer cells preferentially to normal cells, the so-called "therapeutic window" which accepts significant adverse effects for even marginal slowing of tumor growth. Specific treatments that spare normal cells are urgently needed.

Cancer cells and, indeed, disease cells generally, are different from normal cells in many ways, including a propensity for protein misfolding, intracellularly and at the cell surface. Such misfolded proteins may be the consequence of germ cell or somatic mutation, chromosomal translocation or aneuploidy, mutagenic effects of chemotherapy or radiation therapy, titration of chaperones, molecular crowding in the endoplasmic reticulum and other secretory compartments including the cell surface, aberrant glycosylation and trafficking, impaired clearance and/or degradation, environmental stressors or allosteric influences relevant to the tumor bed (such as lowered pH or increased ligand concentration), and post-translational modifications including oxidation and nitration of select residues. All or some of these factors relevant to cancer contribute to greater dynamic fluctuation and net solvent exposure of specific regions of proteins which are normally rarely accessible in non-cancerous cells. Antibody recognition of these abnormally exposed protein motifs, designated Disease Specific Epitopes (DSE), can serve as a diagnostic cancer marker or cancer treatment target, and provide insight into abnormal cell growth in cancer and other diseases.

Cashman et al have described the principles to be applied when targeting a misfolded protein presented by a disease cell, in WO 2010/04020 published Apr. 15, 2010. This publication describes an algorithm that can be applied to a surface protein of interest, to identify "hot spots" or DSEs that while buried within the protein in its normal conformation are likely to become exposed when the protein misfolds. This approach has been applied successfully to many different targets, by producing antibodies to the predicted DSEs and demonstrating that inhibition of the antibody target yields a desired effect on disease cells. It has been shown, for instance, that cancer cells present misfolded surface proteins that include the prion protein, PrP, (see US 2013-0330275) and that eradication of cancer cells is achieved when those cells are incubated with an antibody that binds to an epitope unique to misfolded PrP (see WO 2013/185215).

The Cashman et al publication also proposes various DSE targets for each of a number of different target proteins commonly associated with disease. These include the protein known as the Fas receptor, or FasR. FasR is a member of the tumour necrosis factor receptor superfamily which is a complex group of cell surface proteins that regulate various cell functions. FasR and its ligand, Fas, are involved particularly in caspase-mediated programmed cell death (apoptosis).

In U.S. Pat. No. 6,846,637, IMED describes specific FAS peptides that are useful to raise therapeutic FAS antibodies. Merck's WO 2004/113387 similarly describes FAS peptides that are produced as Fc fusions and are based on specific FAS domains. Treatment of high grade glioma using FAS antibodies, and of CNS-based inflammatory disorders using any FAS inhibitor, has been proposed by the University of Heidelberg, in their WO 2008/080623 and WO 2010/006772, respectively. Inflammation is treated, according to U.S. Pat. No. 7,510,710, using a combination of FAS antibody and a fatty acid metabolism inhibitor In U.S. Pat. No. 6,015,559, Immunex describes antibodies that bind FAS extracellular domain (see also U.S. Pat. No. 5,830,469). Sankyo describes a specific FAS antibody that is humanized and designated HFE7 A, whereas Human Genome Sciences describes antibodies that bind to variants of the parental FAS-related TNFR6 protein (see U.S. Pat. No. 7,534,428, U.S. Pat. No. 7,285,267 and U.S. Pat. No. 7,186,800).

The FAS system is a highly intricate signalling complex that requires on-going elucidation of its interactions in order to understand its role(s) in apoptosis and proliferation. To this end, it would be useful to provide reagents that include FAS-binding ligands and antibodies that permit detection and/or inhibition of FAS, particularly in disease states.

SUMMARY OF THE INVENTION

The present invention provides antibodies that bind selectively to misfolded human FasR, and misfolded FasR-binding fragments and conjugates of such antibodies. In other aspects, there are provided pharmaceutical compositions that comprise these products, and methods for their medical applications in diagnosis and treatment of conditions in which aberrant FasR is implicated. In addition, there is provided a method for producing the antibodies, fragments and conjugates. In a further aspect, antibody production is achieved by administration of an immunogen or vaccine that elicits production of the antibody in a recipient to be treated. The immunogen and vaccine thus constitute further valuable aspects of the present invention.

These and other aspects of the invention are now described in greater detail with reference to the accompanying drawings in which:

DETAILED DESCRIPTION OF THE INVENTION

Figure 1A:
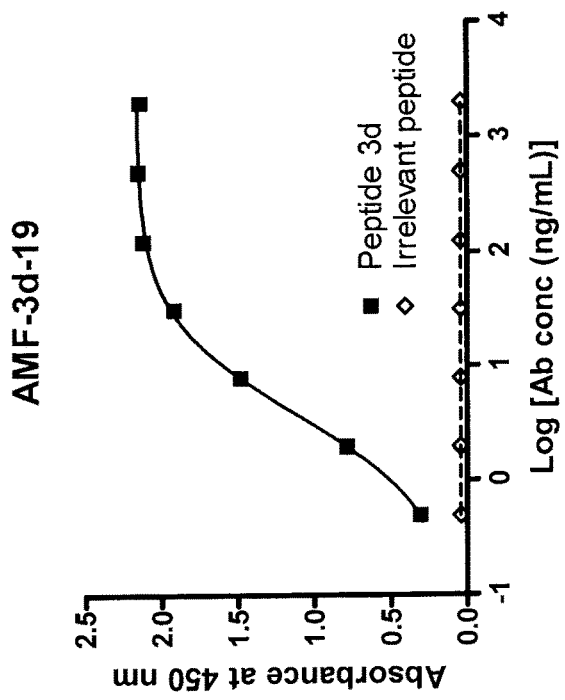
FIG. 1 shows anti-peptide binding of two anti-Fas monoclonal antibodies. (A) AMF-3a-118. (B) AMF-3d-19. Each antibody was evaluated for binding to a BSA-irrelevant peptide (open diamonds) and BSA-specific peptide (filled squares)
Figure 1B:
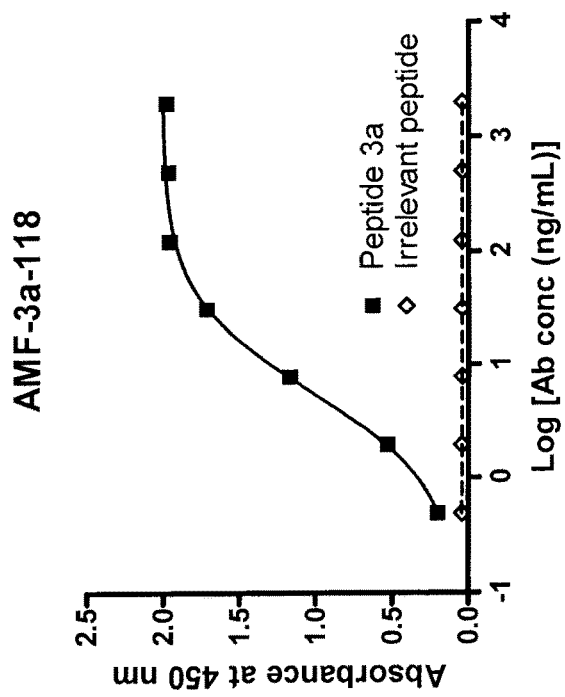
Figure 2A:
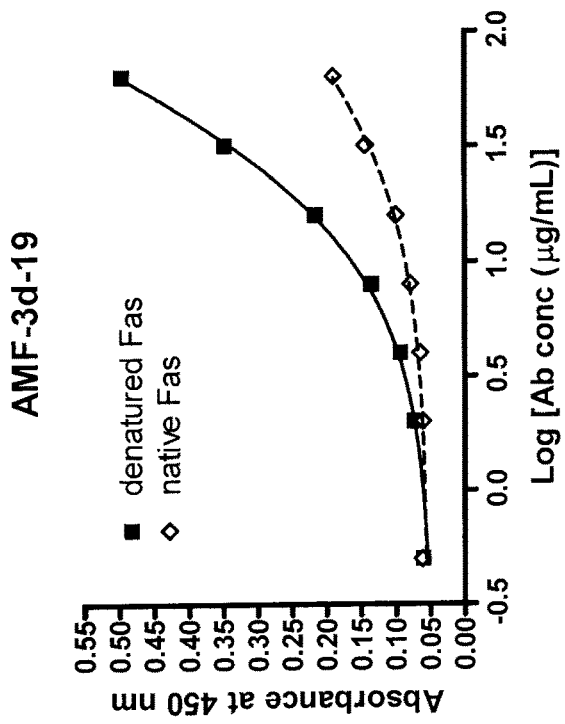
FIG. 2 shows anti-PrP binding of two anti-Fas monoclonal antibodies. (A) AMF-3a-118. (B) AMF-3d-19. Each antibody was evaluated for binding to denatured recombinant Fas (filled squares) and His-tagged native Fas (open diamonds)
Figure 2B:
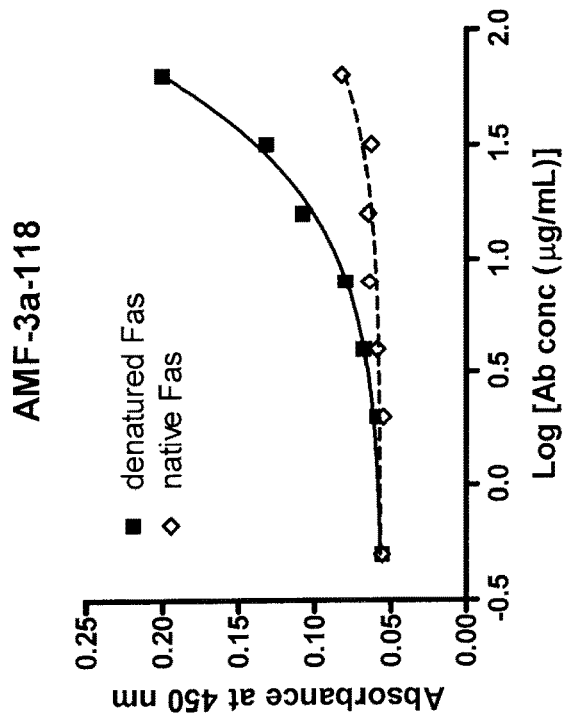
Figure 3:
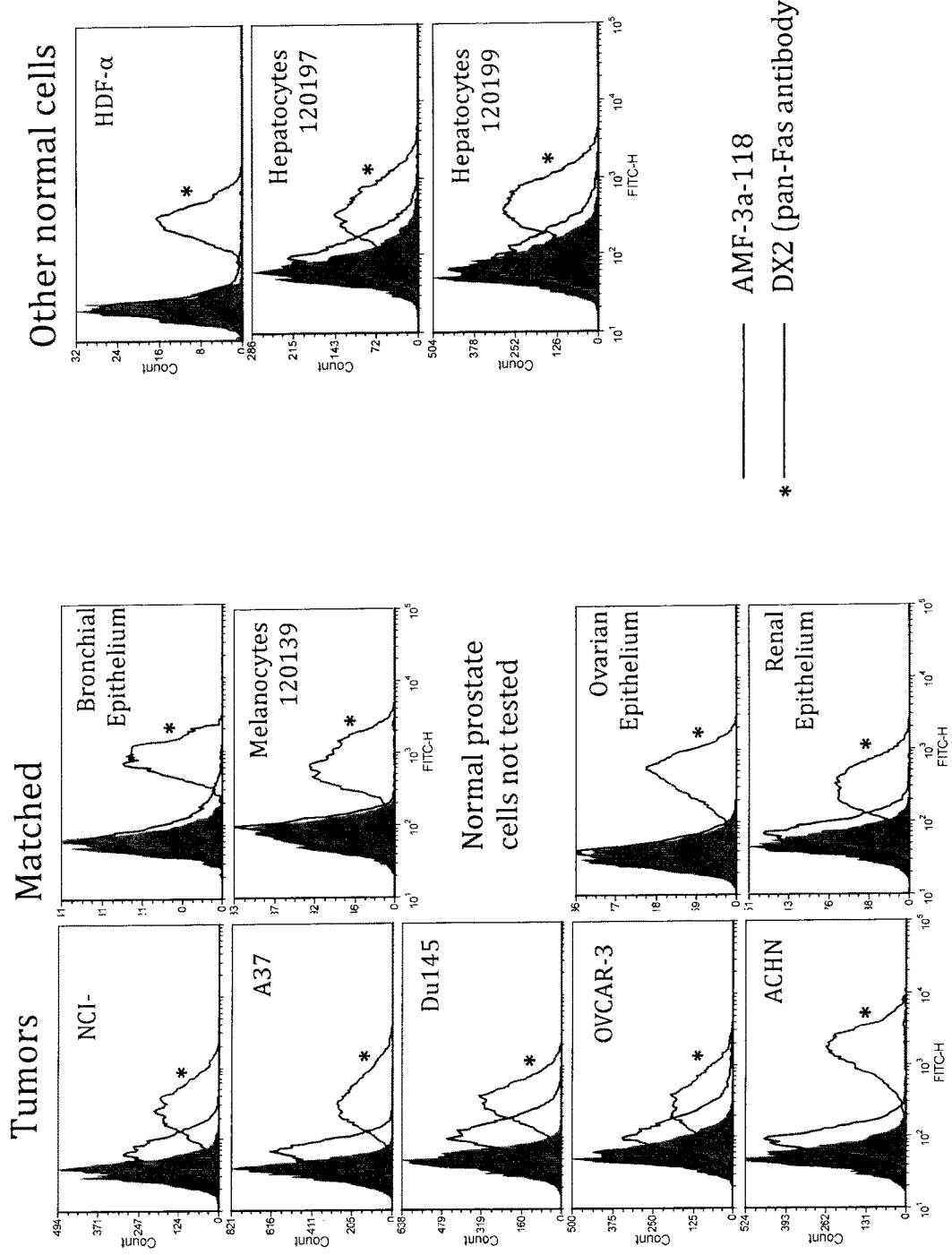
FIG. 3 shows binding of AMF-3a-118 to tumor and normal cells. AMF-3a-118 antibody (80 µg/mL) and DX2, a control anti-Fas antibody (10 µg/mL) were incubated with various cells. Antibody binding was detected using an anti-rabbit IgG-AF488 or anti-mouse IgG-AF488 secondary antibody, followed by fluorescence evaluation by flow cytometry (BD FACS Canto II)
Figure 4:
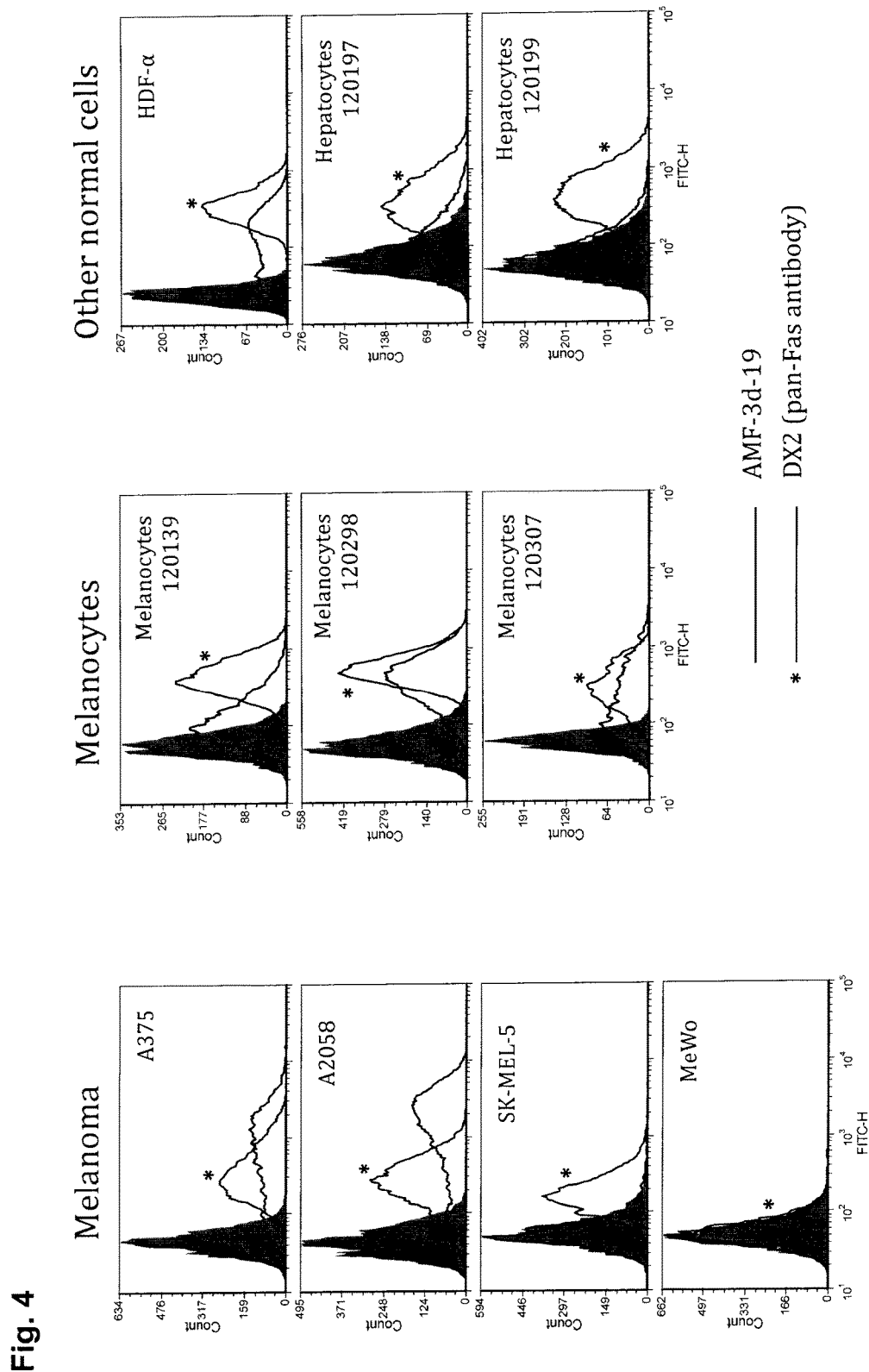
FIG. 4 shows binding of AMF-3d-19 to tumor and normal cells. AMF-3d-19 antibody (10 µg/mL) and DX2, a control anti-Fas antibody (10 µg/mL) were incubated with various cells. Antibody binding was detected using an anti-rabbit IgG-AF488 or anti-mouse IgG-AF488 secondary antibody, followed by fluorescence evaluation by flow cytometry (BD FACS Canto II)

Fas receptor (FasR) is known also as human tumour necrosis factor superfamily member 6 receptor (hTNFRSM6), and as CD95, and is implicated in cancer. Its sequence is set out in UniProtKB/SwissProt #P25445, and the mature form is constituted by residues 26-335. It is a death receptor on the surface of cells that leads to caspase-mediated programmed cell death (apoptosis).

The present invention provides and exploits agents that bind uniquely to misfolded FasR, and particularly, in embodiments of the present invention, to an epitope comprised by any one of the peptides shown below:

| Peptide | Residues | Sequence | ID No. |
|---|---|---|---|
| Human FasR | 52-60 | LHHDGQFCH | 2 |
| (hTNFRSM6) | 70-80 | ARDCTVNGDEP | 3 |
| P25445 residues | 105-111 | RLCDEGH | 4 |
| 26-335 | 136-142 | NSTVCEH | 5 |
| | 167-189 | EEPSRSNLGWLCL | 6 |

In a particular embodiment, the binding agent binds selectively to a FasR epitope that comprises an LHHDGQFCH sequence (SEQ ID No. 2). In an alternative embodiment, the binding agent binds selectively to a FasR epitope that comprises an NSTVCEH sequence (SEQ ID No. 5).

Also provided herein as binding agents that bind selectively to misfolded FasR, are antibodies that bind to one of the two peptide sequences just recited. In particular, and in one of its aspects, the present invention provides an antibody designated AMF 3a-118, the antibody having been raised against the LHHDGQFCH in the manner exemplified herein. The heavy chain of the 3a-118 antibody has SEQ ID No. 29. The light chain of the 3a-118 antibody has SEQ ID No. 31. The heavy chain variable region of the 3a-118 antibody has SEQ ID No. 30. The light chain variable region of the 3a-118 antibody has SEQ ID No. 32. The misfolded FasR binding site presented by this antibody comprises the following CDRs:

For the heavy chain

| CDR1 | DSRVS | (SEQ ID No. 33) |
|---|---|---|
| CDR2 | IVGIGWNIYHANWAKG | (SEQ ID No. 34) |
| CDR3 | GLGGGTVI | (SEQ ID No. 35) |

For the light chain

| CDR1 | QSSESVYKNNYLS | (SEQ ID No. 36) |
|---|---|---|
| CDR2 | EASKLAS | (SEQ ID No. 37) |
| CDR3 | LGEFSCYSGDCGT | (SEQ ID No. 38) |

In addition, the present invention provides an antibody designated AMF 3d-19, the antibody having been raised against the NSTVCEH sequence in the manner exemplified herein. The heavy chain of the 3d-19 antibody has SEQ ID No. 43. The light chain of the 3d-19 antibody has SEQ ID No. 45. The heavy chain variable region of the 3d-19 antibody has SEQ ID No. 44. The light chain variable region of the 3d-19 antibody has SEQ ID No. 46. The misfolded FasR binding site presented by this antibody comprises the following CDRs:

For the heavy chain

| CDR1 | RNAIN | (SEQ ID No. 47) |
|---|---|---|
| CDR2 | IIGSSGVTYYASWAKG | (SEQ ID No. 48) |
| CDR3 | NLYTGGSNDNL | (SEQ ID No.49) |

For the light chain

| CDR1 | QASKSVYNNVQLS | (SEQ ID No. 50) |
|---|---|---|
| CDR2 | YASTLAS | (SEQ ID No. 51) |
| CDR3 | AGGYSSSSDNA | (SEQ ID No. 52) |

It will thus be appreciated that the binding agent useful in the present methods can be any antibody or a fragment thereof that binds selectively to an epitope unique to misfolded FasR, and particularly to the epitopes identified above by SEQ ID Nos. 2 and 5.

The antibodies that bind selectively to the misfolding specific epitopes may be either polyclonal or monoclonal, of the IgG or IgM class, and may be derived from any mammal, particularly goats, rabbits or mice, or by recombinant methods. More generally, it will be appreciated that antibodies useful in the present invention include the various intact forms including polyclonal antibodies, monoclonal antibodies, and recombinant antibodies including those having human constant regions such as chimeric antibodies, humanized antibodies as well as fully human antibodies and bispecific or multispecific antibodies.

In an embodiment, the antibody comprises a human constant region.

The chimeric antibodies comprise a portion of the heavy and/or light chain that is homologous with corresponding sequences in antibodies derived from a particular species, or belonging to a particular antibody class or subclass, while the remainder of the chain(s) is homologous with corresponding sequences derived from another species or belonging to a different antibody class. Humanized antibodies are chimeric antibodies that comprise minimal sequence derived from non-human antibody, usually incorporating CDRs from a non-human antibody into a human antibody framework, which may further be altered to incorporate non-human residues that restore and enhance antigen binding. The "fully" human antibodies can be produced in a non-human host using various techniques that are now established, including through the use of phage display libraries, and particularly by introducing human immunoglobulin loci into transgenic animals such as mice in which the endogenous immunoglobulin genes have been partially or completely inactivated. Upon challenge, human antibodies are produced which closely resemble that seen in humans in most respects, including gene rearrangement, assembly and antibody repertoire.

Using phage display antibodies are displayed on the surface of phage by for example fusing the coding sequence of antibody variable regions to the phage minor coat protein pIII. Antibodies can be selected using the phage displayed antibody libraries (including synthetic antibody libraries wherein synthetic diversity is introduced at solvent-exposed positions within the heavy chain complementarity-determining regions) by a series of cycles of selection on antigen. Antibody genes can be cloned simultaneously with selection and further engineered for example by increasing their affinity or modulating their specificity or their effector function (by recloning into a full-length immunoglobulin scaffold e.g. making a recombinant human antibody).

In an embodiment, the antibody is a recombinant or synthetic antibody, for example the human antibody is a recombinant or synthetic human antibody.

The antibodies may be of any useful class, including IgA, IgD, IgE, IgG and IgM, and isotypes including IgG1, IgG2, IgG3, and IgG4. The constant region (Fc) of the antibodies can also be engineered or conjugated to provide altered effector function, thereby to enhance antibody dependent cell-mediated cytotoxicity (ADCC) and/or complement dependent cytotoxicity (CDC) activity.

For therapeutic use, in embodiments, the antibody desirably is itself toxic to the cells presenting the target FasR epitope. To this end, the antibody desirably incorporates an Fc region having effector function, such as ADCC activity and/or CDC activity. In the alternative, and in accordance with other embodiments, the antibody or binding fragment is conjugated with a cytotoxin that is toxic to the cells targeted by the antibody or binding fragment.

The antibodies otherwise can have all of the attributes common to intact antibodies. In embodiments, the present antibodies are of the IgG1 isotype, but they may also be IgG2 or IgG4. Moreover, the isotype of the antibody, as dictated by the constant region, can be manipulated to alter or eliminate the effector function of the resulting antibody. That is, the constant region of the present antibodies is either wild type human antibody constant region, or a variant thereof that incorporates amino acid modifications, i.e., amino acid additions, substitutions or deletions that alter the effector function of the constant region, such as to enhance serum half-life, reduce or enhance complement fixation, reduce or enhance antigen-dependent cellular cytotoxicity and improve antibody stability. The number of amino acid modifications in the constant region is usually not more than 20, such as 1-10 e.g., 1-5 modifications, including conservative amino acid substitutions.

In embodiments, the half-life of the antibody is improved by incorporating one or more amino acid modifications, usually in the form of amino acid substitutions, for instance at residue 252, e.g., to introduce Thr, at residue 254, e.g., to introduce Ser, and/or at residue 256 e.g., to introduce Phe. Still other modifications can be made to improve half-life, such as by altering the CH1 or CL region to introduce a salvage receptor motif, such as that found in the two loops of a CH2 domain of an Fc region of an IgG. Such alterations are described for instance in U.S. Pat. No. 5,869,046 and U.S. Pat. No. 6,121,022.

Altered C1q binding, or reduced complement dependent cytotoxicity, can be introduced by altering constant region amino acids at locations 329, 331 and 322, as described in U.S. Pat. No. 6,194,551. The ability of the antibody to fix complement can further be altered by introducing substitutions at positions 231 and 239 of the constant region, as described in WO94/029351.

Framework modifications can also be made to reduce immunogenicity of the antibody or to reduce or remove T cell epitopes that reside therein, as described for instance by Carr et al in US2003/0153043.

Antibodies can also be altered in the variable region to eliminate one or more glycosylation sites, and/or to improve physical stability of the antibody. For example, in one embodiment, the physical stability of the antibody is improved by substituting the serine at position 228 of the variable region with a proline residue (i.e., the antibody has a variable region comprising a S228P mutation). The S228P alteration significantly stabilizes the antibody structure against the formation of intrachain disulfide bonds. In another embodiment, the variable region is altered to eliminate one or more glycosylation sites resident in the variable region. More particularly, it can be desirable in the sequence of the present antibodies to eliminate sites prone to glycosylation. This is achieved by altering the occurrence of one or more N-X-(S/T) sequences that occur in the parent variable region (where X is any amino acid residue), particularly by substituting the N residue and/or the S or T residue.

Antibodies can be engineered to include a variety of constant regions. In one embodiment, the antibody comprises a constant region the sequence of which corresponds to the constant region of an antibody of human origin, such as a human IgG1 constant region. In a particular embodiment, the constant region is inert for effector function (e.g., essentially devoid of effector function). In a specific embodiment the constant region is a human IgG4 constant region.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In addition, the antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 154316 and EP 401384.

The antibodies and binding fragments are useful both for diagnostic purposes, including in vivo imaging to identify endogenous sites of senescent cells in vivo, and for sample testing to detect senescent cells in vitro. The antibodies and binding fragments are also useful for therapeutic purposes to treat diseases such as cancers in which misfolded FasR+ cells are implicated.

"Selective-binding" agents are agents that bind the target epitope, and bind proteins that present the target epitope in a solvent-accessible orientation, with an affinity that is at least 2 times greater than the affinity with which they bind a different, unrelated epitope, such as 3 times greater, 5 times greater or at least one order of magnitude greater (e.g., at least 2, 3, 4 or 5 orders of magnitude greater For instance, the binding affinity of an antibody that binds misfolded FasR is preferably at least twice its binding affinity for normal FasR. Relative binding affinities can be determined, and the antibody so selected, on the basis of assays and techniques that generally are well established in the art for this purpose.

In an embodiment, the antibody affinity has an EC50 which is at least $10^{-6}$ M, at least $10^{-7}$ M, at least $10^{-8}$ M, or at least $10^{-9}$ M.

Antibodies that bind selectively to the target epitopes can be produced by techniques including immunization, or by alternative approaches such as by the application of phage display and other systems that use high throughput to identify complementarity determining regions (CDR) or other sequences that bind to the target epitope. It is not essential that the resulting antibody has been first raised in vivo. More particularly, to produce suitable antibodies, amino acid sequences that constitute epitopes can be useful per se to raise antibodies that bind specifically to them, provided they are endowed per se with the immunogenicity required to raise antibody in the selected antibody production host. For those epitopes that lack such immunogenicity, it is desirable to provide an immunogen that contains the epitope sequence.

As used herein, "immunogen" refers to an immunogenic form of a peptide or other molecule that comprises the epitope, and is represented by the peptide itself when immunogenic per se, or is represented by the peptide in combination with an immunogenicity-enhancing agent. Any of the established agents can be used for this purpose. These agents typically include carrier proteins that can be coupled to the epitope either directly, such as through an amide bond, or indirectly through a chemical linker such as carbodiimide, a cysteine, or any peptide spacer sequence such as a glycine or glycine-serine sequence including Gly4-S. For example, an isolated peptide comprising a given epitope can be conjugated to MAP antigen, OVA antigen, or keyhole limpet hemocyanin (KLH). Its large size makes it very immunogenic, and the large number of lysine residues available for conjugation makes KLH very useful to attach to a polypeptide. The immunogen may further comprise a linker effective to couple the peptide tandemly to another copy of the same or a different peptide corresponding to the same or a different epitope. In another embodiment, the peptides may comprise additional amino acids that enhance the immunogenicity or solubility of the peptide. In one embodiment, the additional amino acids number from 1 to about 10, preferably 1 to 8, more preferably 1 to 5. Importantly the additional residues do not materially affect the conformation of the peptide.

Thus, for antibody production, epitopes that are not themselves immunogenic and do not constitute an immunogen can be rendered so, and provided as an immunogen, by incorporating immune enhancing agents that are either conjugated therewith or coupled covalently.

A composition comprising the immunogen can be prepared for purposes of producing antibodies in a selected host by combining the immunogen with an appropriate vehicle. Such vehicles include Freund's complete adjuvant or other adjuvant or a suitable saline or phosphate buffered saline solution (0.05-1.0%).

Antibodies are then prepared to react against these epitopes when they are in an unstructured state. As noted, each peptide may be conjugated to a carrier protein like KLH to form an immunogen that is injected, optionally in combination with an adjuvant such as Freund's complete adjuvant, into a mammalian production host like a mouse, rat, rabbit, sheep or goat to provoke an immune response that generates antibodies against the peptide. Standard immunization protocols can be used, and the antibodies can be recovered from blood by enrichment against the immunizing agent, as exemplified herein.

The antibodies useful herein are desirably "isolated" antibodies, which refers to an antibody that is substantially free of other antibodies having different antigenic specificities (e.g., an isolated antibody that specifically binds misfolded FasR is substantially free of antibodies that specifically bind antigens other than FasR proteins). An isolated antibody that specifically binds a misfolded human FasR protein may, however, have cross-reactivity to other antigens, such as misfolded FasR proteins from other species. Moreover, an isolated antibody can be substantially free of other cellular material and/or chemicals. An isolated antibody also can be substantially free of other proteins of human origin. In embodiments, the isolated antibody is an exogenous antibody as distinct from an antibody endogenous to an intended recipient.

Thus, in embodiments, the antibody is an intact antibody comprising features common to all natural antibodies, e.g., a heavy chain and a light chain, each chain having a constant region and a variable region, each variable region comprising framework regions (FRs) and complementarity determining regions (CDRs). In the alternative, the antibody is provided as a target-binding fragment, such as a monovalent fragment, Fab, or a bivalent antibody fragment comprising both "arms" of an intact antibody, joined through a linker that can be represented by the hinge region of the antibody or any equivalent. Such fragments include F(ab)2 fragments and any other fragment that retains preference for binding to misfolded FasR. In particular embodiments, the antibody fragment is a F(ab')2 fragment, generated for instance by papain-based digestion of the parent antibody using standard procedures for digestion and subsequent fragment isolation. In the alternative, the fragment can be a so-called single chain Fv (scFv), consisting of the variable light and variable heavy antibody domains joined by an amino acid linker, or a bivalent form of a so-called diabody prepared using a 5 amino acid linker such as SGGGG (SEQ ID NO: 1) between the light and heavy chain variable domains and a C-terminal cysteine modification to GGC to give a final diabody product as VL-SGGGG (SEQ ID NO: 1)-VH-GGC. Still other bivalent fragments can be prepared by coupling the light and heavy chain variable domains through thioether linkages such as bis-maleimidomethyl ether (BMME), N,N'-p-phenylene dimaleimide (PDM and N,N'-bismaleimidohexane BMH), to stabilize the F(ab')2 fragments.

Of course, for antibodies having known protein or gene sequences, the antibody can be produced suitably by recombinant DNA means. For production, there is provided a DNA molecule that encodes the heavy chain of the present antibody, and a DNA molecule that encodes the light chain thereof. The DNA further encodes any suitable signal peptide suitable for expression of a secretable chain precursor that enables proper externalization with folding and disulfide formation to elaborate the desired antibody as a secreted, dimerized and processed protein.

To this end, the present invention provides, in one aspect, polynucleotides that encode the heavy and light chains of the FasR antibodies herein described. In one embodiment, there is provided a polynucleotide comprising a sequence that encodes the light chain variable region of the FasR antibody AMF 3a-118, as set out in SEQ ID No. 42. Also provided, in another embodiment, is a polynucleotide comprising a sequence that encodes the heavy chain variable region of the FasR antibody AMF 3a-118, as set out in SEQ ID No. 40.

In more specific embodiments, the present invention provides a polynucleotide that encodes the entire light chain (SEQ ID No. 41) and a polynucleotide that encodes the entire heavy chain (SEQ ID No. 39) of misfolded FasR antibody AMF 3a-118 antibody.

The present invention also provides, in another aspect, polynucleotides that encode the light chain variable region of the FasR antibody AMF 3d-19, as set out in SEQ ID No. 56, and a polynucleotide comprising a sequence that encodes the heavy chain variable region of the FasR antibody AMF 3d-19, as set out in SEQ ID No. 54.

In more specific embodiments, the present invention provides a polynucleotide that encodes the entire light chain (SEQ ID No. 55) and a polynucleotide that encodes the entire heavy chain (SEQ ID No. 53) of the misfolded FasR antibody AMF 3d-19

It will be appreciated that polynucleotide equivalents also can be used, in which synonymous codons are replaced within the sequences provided, to produce the present antibodies.

In an embodiment, the nucleic acid is a cDNA. In another embodiment, the nucleic acid is a codon optimized cDNA.

In embodiments, there are also provided vectors that comprise polynucleotides that encode the heavy chain or the variable region thereof and that encode the light chain or the variable region thereof. To express the antibodies, the polynucleotides are incorporated operably within expression vectors, i.e. operatively linked to transcriptional and translational control sequences. Expression vectors include plasmids, retroviruses, cosmids, and the like. The expression vector and expression control sequences are chosen to be compatible with the expression host cell used. The antibody light chain gene and the antibody heavy gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region, and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Polynucleotides encoding the heavy chain and/or the light chain, and vectors comprising these can be used for transformation of a suitable mammalian host cell. Methods for introduction of heterologous polynucleotides into mammalian calls include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, polynucleotides may be introduced into mammalian cells by viral vectors.

Mammalian cell lines useful as hosts for expression of the antibody-encoding polynucleotides include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., HepG2), A549 cells, 3T3 cells, and a number of other cell lines. In a specific embodiment, the polynucleotides are expressed in a HEK293 host. Mammalian host cells include human, mouse, rat, dog, monkey, pig, goat, bovine, horse, and hamster cells. Cell lines of particular preference are selected through determining which cell lines have high expression levels. Other cell lines that may be used are insect cell lines, such as S19 cells, amphibian cells, bacterial cells, plant cells and fungal cells. When recombinant expression vectors encoding the heavy chain or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The antibodies of the invention can be obtained as human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) Nature 368(6474): 856-859). Accordingly, the mice exhibit reduced expression of mouse IgM or κ and in response to immunization, the introduced human heavy and light chain transgenes undergo class switching and somatic mutation to generate high affinity human IgGκ monoclonal antibodies (Lonberg et al. (1994), supra; reviewed in Lonberg (1994) Handbook of Experimental Pharmacology 113: 49-101; Lonberg, N. and Huszar, D. (1995) Intern. Rev. Immunol. 13: 65-93, and Harding and Lonberg (1995) Ann. N.Y. Acad. Sci. 764:536-546). Preparation and use of the HuMAb Mouse®, and the genomic modifications carried by such mice, is further described in Taylor et al. (1992) Nucleic Acids Research 20:6287-6295; Chen et al. (1993) International Immunology 5: 647-656; Tuaillon et al. (1993) Proc. Natl. Acad. Sci. USA 90:3720-3724; Choi et al. (1993) Nature Genetics 4:117-123; Chen et al. (1993) EMBO J. 12: 821-830; Tuaillon et al. (1994) J. Immunol. 152:2912-2920; Taylor et al. (1994) International Immunology 6: 579-591; and Fishwild et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, the human antibodies are raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478. A modified form of this mouse, which further comprises a homozygous disruption of the endogenous FcγRIIB receptor gene, is also described in PCT Publication WO 02/43478 and referred to herein as a "KM/FCGR2D Mouse®." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075,181; 6,114,598; 6,150,584 and 6,162,963). Further embodiments include "TC mice" (Tomizuka et al. (2000) Proc. Natl. Acad. Sci. USA 97:722-727) and cows carrying human heavy and light chain transchromosomes (Kuroiwa et al. (2002) Nature Biotechnology 20:889-894; PCT Publication WO 02/092812). The contents of these patents and publications are specifically incorporated herein by reference in their entirety.

Human monoclonal antibodies also can be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

Antibodies of the invention also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or γ-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because mammalian cells are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells, HEK293 cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Thus, in another aspect, there is provided a cellular host that incorporates expressibly therein a polynucleotide that encodes the light chain, or the light chain variable region, of the misfolded human FasR antibody designated 3a-118, the polynucleotides having SEQ ID No. 41 (entire light chain) or SEQ ID No. 42, respectively. In other embodiments, there is provided a cellular host that incorporates expressibly therein a polynucleotide that encodes the heavy chain, or the heavy chain variable region, of the misfolded human FasR antibody designated 3a-118, having SEQ ID No. 39 (entire heavy chain) or SEQ ID No. 40 (heavy chain variable region). In a further embodiment, there is provided a cellular host that incorporates expressibly therein both the heavy and light chain-encoding polynucleotides just recited, in either fully length form or in the form of variable region-encoding polynucleotides. In a still further embodiment, there comprises the step of culturing the transfected cellular host, thereby to produce the desired 3a-118 antibody.

Further, in embodiments, there is provided a cellular host that incorporates expressibly therein a polynucleotide that encodes the light chain, or the light chain variable region, of the misfolded human FasR antibody designated 3a-118, the polynucleotides having SEQ ID No. 41 (entire light chain) or SEQ ID No. 42 In other embodiments, there is provided a cellular host that incorporates expressibly therein a polynucleotide that encodes the entire heavy chain SEQ ID No. 39), or the heavy chain variable region (SEQ ID No. 40), of the misfolded human FasR antibody designated 3a-118. In a further embodiment, there is provided a cellular host that incorporates expressibly therein both the heavy and light chain-encoding polynucleotides just recited, in either fully length form or in the form of variable region-encoding polynucleotides. In a still further embodiment, there comprises the step of culturing the transfected cellular host, thereby to produce the desired 3a-118 antibody.

Also, in embodiments, there is provided a cellular host that incorporates expressibly therein a polynucleotide that encodes the light chain, or the light chain variable region, of the misfolded human FasR antibody designated 3d-19, the polynucleotides having SEQ ID No. 55 (entire light chain) or SEQ ID No, 56, respectively. In other embodiments, there is provided a cellular host that incorporates expressibly therein a polynucleotide that encodes the heavy chain, or the heavy chain variable region, of the misfolded human FasR antibody designated 3d-19, having SEQ ID No. 53 (entire heavy chain) or SEQ ID No. 54 (heavy chain variable region). In a further embodiment, there is provided a cellular host that incorporates expressibly therein both the heavy and light chain-encoding polynucleotides just recited, in either fully length form or in the form of variable region-encoding polynucleotides. In a still further embodiment, there comprises the step of culturing the transfected cellular host, thereby to produce the desired 3d-19 antibody.

Further, in embodiments, there is provided a cellular host that incorporates expressibly therein a polynucleotide that encodes the light chain, or the light chain variable region, of the misfolded human FasR antibody designated 3d-19, the polynucleotides having SEQ ID No. 55 (entire light chain) or SEQ ID No. 56 In other embodiments, there is provided a cellular host that incorporates expressibly therein a polynucleotide that encodes the entire heavy chain SEQ ID No. 53), or the heavy chain variable region (SEQ ID No. 54), of the misfolded human FasR antibody designated 3d-19. In a further embodiment, there is provided a cellular host that incorporates expressibly therein both the heavy and light chain-encoding polynucleotides just recited, in either fully length form or in the form of variable region-encoding polynucleotides. In a still further embodiment, there comprises the step of culturing the transfected cellular host, thereby to produce the desired 3d-19 antibody.

For use in the methods of the present invention, the antibodies and their binding fragments can be conjugated with other agents that are useful for the intended purpose, e.g., either diagnostic use or medical treatment. Agents appropriate for treating disease include cytotoxic agents or toxins that include chemotherapeutics and radiotherapeutics. For diagnostic purposes, appropriate agents are detectable labels that include radioisotopes or fluorescent markers for whole body imaging, and radioisotopes, enzymes, fluorescent labels and the like for sample testing.

For diagnostics, the detectable labels can be any of the various types used currently in the field of in vitro diagnostics, including particulate labels including biotin/streptavidin, metal sols such as colloidal gold, isotopes such as 1125 or Tc99 presented for instance with a peptidic chelating agent of the N2S2, N3S or N4 type, chromophores including fluorescent markers such as FITC and PE, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

For therapy, the cytotoxin can be conjugated with the antibody or binding fragment through non-covalent interaction, but more desirably, by covalent linkage either directly or, more preferably, through a suitable linker. In a preferred embodiment, the conjugate comprises a cytotoxin and an antibody.

Immunoconjugates of the antibody and cytotoxin are made using a variety of bifunctional protein coupling agents such as SMCC, N-succinimidyl-3-(2-pyridyldithiol) propionate, iminothiolane, bifunctional derivatives of imidoesters such as dimethyl adipimidate HCl, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). Carbon-14-labeled 1-isothiocyanobenzyl-3-methyldiethylene triaminepentaacetic acid (MX-DTPA) is a chelating agent suitable for conjugation of radionuclide to the antibody.

The cytotoxin component of the immunoconjugate can be a chemotherapeutic agent, a toxin such as an enzymatically active toxin of bacterial, fungal, plant or animal origin such as urease, or fragments thereof, or a small molecule toxin, or a radioactive isotope such as 212Bi, 131I, 131In, 111In, 90Y, and 186Re, or any other agent that acts to inhibit the growth or proliferation of a senescent cell.

Chemotherapeutic agents useful in the generation of such immunoconjugates include maytansinoids including DM-1 and DM-4, adriamycin, doxorubicin, epirubicin, 5-fluoroouracil, cytosine arabinoside ("Ara-C"), cyclophosphamide, thiotepa, busulfan, cytoxin, taxoids, e.g. paclitaxel, and docetaxel, taxotere, methotrexate, cisplatin, melphalan, vinblastine, bleomycin, etoposide, ifosamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included are hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *phytolaca Americana* proteins (PAPI, PAPII, and PAP-S), *momordica charantia* inhibitor, curcin, crotin, *sapaonaria, officinalis* inhibitor, gelonin, saporin, mitogellin, restrictocin, phenomycin, enomycin, and the tricothcenes. Small molecule toxins include, for example, calicheamicins, maytansinoids including DM-1 and DM-4, palytoxin and CC 1065.

In an embodiment, the binding agent, optionally an antibody and/or binding fragment thereof, optionally conjugated to a toxin or a label or the nucleic acid is comprised in a composition. In an embodiment the composition comprises a diluent such as a saline solution for example phosphate buffered saline solution (0.05-1.0%).

The present invention also provides, for therapeutic use, a vaccine comprising any immunogenic form of an epitope that is unique to a misfolded form of human FasR, to treat subjects presenting with disease that is associated with cells presenting that misfolded form of the protein. Such vaccines with comprise carriers that are nontoxic to recipients at the dosages and concentrations employed. Ordinarily, the preparation of such compositions entails combining the particular vaccine antigen (immunogen) with saline, buffers, antioxidants such as ascorbic acid, low molecular weight (less than about 10 residues) polypeptides, proteins, amino acids, carbohydrates including glucose or dextrins, or chelating agents such as EDTA, glutathione and other stabilizers and excipients. Such compositions may be in suspension, emulsion or lyophilized form and will be pharmaceutically acceptable; i.e., suitably prepared and approved for use in the desired application. Preferred peptide vaccine compositions also comprise an adjuvant. DNA adjuvants are preferred for human use. The peptides may be formulated as fusions with other immunogenic peptides from the same or a different pathologic entity. Peptides may be synthesized as fusions of the epitopes identified herein with one or more T-helper epitope such as PADRE (SEQ ID NO: 57) or certain known tetanus peptides. Spacer peptides also may comprise part of these fusions. Materials having adjuvant activity are well known. Currently, however, Alum (Al(OH)$_3$), and similar aluminium gels are the only adjuvants licensed for human use. Other materials are also known to have adjuvant activity, and these include: Freund's complete adjuvant, a water-in-mineral-oil emulsion which contains killed, dried mycobacteria in the oil phase; Freund's incomplete adjuvant, a weaker formulation without the mycobacteria; saponin, a membrane active glucoside extracted from the tree *Quillia saponaria*; nonionic block copolymer surfactants, non metabolised synthetic molecules which tend to bind proteins to cell surfaces; ISCOMS, lipid micelles incorporating Quil A (saponin) which mimic, in physical terms, infectious particles; and muramyl dipeptide, a leukocyte stimulatory molecule that is one of the active components of killed mycobacteria.

It will be appreciated that the vaccines noted above may comprise, instead of the epitope designated above, a variant thereof that incorporates 1, 2 or 3, amino acid additions, substitutions or deletions. Particularly the epitope may be a variant that has been truncated or extended to consist of 6, 7, or 8 amino acids, preferably 7 amino acids, and that incorporates up to 2, usually 1, amino acid substitution, for instance in which an amino acid is replaced by an oxidized form thereof, or an enantiomeric alternative thereof. It is apparent to those skilled in the art that substitution of certain amino acids in these epitopes will not affect immunoreactivity toward the epitopes. For example, substitution of leucine by isoleucine or valine and all combinations thereof is unlikely to alter the sensitivity of an antibody raised against this epitope. Thus all epitopes capable of generating antibodies reactive to the epitopes listed above for the purpose of selectively identifying misfolded human FasR are aspects of this invention.

It may also be desirable to derivatize amino acids present in the epitopes to obtain a more robust immune response or more selective reactivity toward the misfolded form. For example, a cysteine that on misfolding of its host protein may become oxidatively derivatized to cysteine sulfinic acid or cysteine sulfonic acid (cysteic acid). Thus antibodies against a free peptide containing, for example, a cysteic acid residue in place of cysteine are potentially more specific to the misfolded form of the protein. In general, candidate epitopes identified according to the methods described herein and containing derivatives of their constituent amino acids are an aspect of the present invention.

For epitopes containing proline, it may be desirable to prepare antigen peptides containing proline analogues that are fixed in the cis- or trans-configuration. Such analogues have been described previously (Scheraga et al, J Am Chem Soc 121 (49), 11558 (1999); Wang et al, J Org Chem 68 (6), 2343 (2002)). Unlike the other amino acids, for which there is a prohibitively large energy difference between the cis- and trans-amide bond stereoisomers, proline in unstructured peptides is able to interconvert between a cis- and trans-geometry on a relatively rapid time scale. When a proline is incorporated into the folded protein, steric interactions lock it into only one of the two possible conformers, but on unfolding it is free to racemerize. By raising antibodies against peptides incorporating a proline analogue with the opposite stereochemistry to that present in the native structure, the selectivity of the antibody for the unfolded state is much increased. Thus epitope peptides predicted by the method and incorporating cis- or trans-analogues of proline are an aspect of this invention.

In therapeutic use, the antibodies and corresponding fragments and conjugates that bind selectively to misfolded FasR, and vaccines that elicit such antibodies, can be used to treat subjects presenting with or at risk for a disease associated with aberrant FasR folding and signalling including particularly various forms of cancer. The terms "treat", "treatment," "treating", "therapeutic use," or "treatment regimen" encompass prophylactic, palliative, and therapeutic modalities of administration of the compositions of the present invention, and include any and all uses of the present products that remedy a disease state, condition, symptom, sign, or disorder caused or associated with, either directly or indirectly, a cell presenting a misfolded form of FasR, including an inflammation-based pathology, infectious disease, allergic response, hyperimmune response, or other symptom to be treated, or which prevents, hinders, retards, or reverses the progression of symptoms, signs, conditions, or disorders associated therewith.

The term "subject" generally refers to mammals and other animals including humans and other primates, companion animals, zoo, and farm animals, including, but not limited to, cats, dogs, rodents, rats, mice, hamsters, rabbits, horses, cows, sheep, pigs, elk or other ungulates, goats, poultry, etc. A subject includes one who is to be tested, or has been tested for prediction, assessment or diagnosis of a disease or disorder associated with cell senescence. The subject may have been previously assessed or diagnosed using other methods, such as those in current clinical practice, or may be selected as part of a general population (a control subject). A subject may be a transgenic animal, e.g. a rodent, such as a mouse, that produces a target protein especially in misfolded form, or is lacking expression thereof (e.g. a 'knock-out' mouse). For example, the subject may a transgenic mouse overexpressing a normal form of the target protein or may be a wild-type mouse or hamster that has been infected with a misfolded form of the target protein.

For treatment, the binding agent, such as antibody induced by the immunogen used for active immunization and the antibody used for passive immunization are used in "effective amounts". These are amounts useful, in a treatment regimen, to reduce the effect of the senescent cells that present the misfolded protein target. It will be apparent that the present invention is applicable to a wide variety of diseases, and that the particular amount and treatment regimen effective to reduce the effect of the endogenous protein will vary with each disease or condition, in accordance with established clinical practice.

In addition to such vaccines, the present invention provides for the therapeutic use of binding agents such as antibodies in the treatment of subjects presenting with the conditions noted above, including conditions/diseases related by the presence of the given misfolded protein. For treatment, antibody that binds selectively to the target epitope is administered as a pharmaceutical composition, comprising the antibody and a pharmaceutically acceptable carrier, in dosage form.

Also provided in another aspect, is a pharmaceutical composition comprising a binding agent that selectively binds misfolded FasR disease cells in an amount effective to reduce the number of such cells for use in treating a subject presenting with disease cells having a misfolded FasR phenotype, wherein the binding agent binds selectively to FasR having a misfolded conformation.

Yet a further aspect includes a pharmaceutical composition comprising a binding agent that selectively binds FasR having a misfolded conformation.

For antibodies, fragments and conjugates, the dosage form is optionally a liquid dosage form. Antibody solutions can be prepared in water suitably mixed with a surfactant such as hydroxypropylcellulose or an emulsifier such as polysorbate. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. Formulations optionally contain excipients including, but not limited to, a buffering agents, an anti-oxidant, a stabilizer, a carrier, a diluent, and an agent for pH adjustment. The pharmaceutical forms suitable for injectable use include sterile aqueous solutions or dispersion and sterile powders for the extemporaneous preparation of sterile injectable solutions or dispersions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

In treatment, the dose of antibody optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight.

For example, depending on the type and severity of the disease, about 1 µg/kg to 15 mg/kg (e.g., 0.1-20 mg/kg) of antibody or conjugate is a candidate dosage for administration to the patient, whether, for example, by one or more separate administrations, or by continuous infusion. A typical daily dosage is in the range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit closes can be in the range, for instance of about 5 mg to 500 mg, such as 50 mg, 100 mg, 150 mg, 200 mg, 250 mg and 300 mg. The progress of therapy is monitored by conventional techniques and assays.

Therapeutic use of an antibody according to the present invention entails antibody administration, by injection or infusion, to subjects presenting with a disease in which cells or fluids present the epitope targeted by the antibody, i.e., in which the misfolded target protein is present. Subjects that would benefit from treatment can be identified by their clinical features, together with examination of tissue samples or bodily fluids to identify cells that present the epitope targeted by the antibody, as discussed infra.

For treatment with a vaccine, subjects are immunized on a schedule that can vary from once a day, to once a week, to once a month, to once a year, to once a decade. A typical regimen includes an immunization followed by booster injections at 6 weekly intervals. Another regimen consists of immunization followed by booster injections 1, 2 and 12 months later. Alternatively, booster injections will vary depending on the immune response and the physiological condition of the subject. For immunization, the epitope-containing immunogen can be administered in a dose that ranges from about 0.0001 microgram to 10 grams, about 0.01 microgram to about 1 gram, about 1 microgram to about 1 mg, and about 100 to 250 micrograms per treatment. In one embodiment the timing of administering treatment is at one or more of the following: 0 months, 2 months, 6 months, 9 months, and/or 12 months. In one regimen, the dosing is at 2, 6, 9, and 12 months following the first immunization. In another regimen, the dosing is at 2 and 4 weeks following the first immunization, and then monthly afterwards. In an alternative regimen, the dosing varies depending on the physiological condition of the subject and/or the response to the subject to prior immunizations. The route of administration optionally includes, but is not limited to, intramuscular and intraperitoneal injections. In one embodiment the composition is injected into the deltoid muscle.

The vaccine composition itself can further comprise adjuvants. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

The active ingredients to be used for in vivo administration will be sterile. This is readily accomplished by filtration through sterile filtration membranes.

Sustained-release preparations may be prepared. Suitable examples of sustained-release include semipermeable matrices of solid hydrophobic polymers containing the antibody, which matrices are in the form of shapes articles, e.g., films or microcapsules. Examples of sustained-release matrices include polyesters, hydrogels (for example, poly (2-hydroxyethyl-methacrylate), polylactides (U.S. Pat. No. 3,773, 919), copolymers of L-glutamic acid and ethyl-L-glutamate, non-degradable ethylene-vinyl acetate, degradable lactic acid-glycolic acid copolymers such as injectable microspheres composed of lactic acid-glycolic acid copolymer and leuprolide acetate, and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Diagnostically useful compositions comprising the antibody will incorporate a carrier suitable for diagnostic purposes, such as a solution of saline or buffered saline including phosphate buffered saline, together with any desired stabilizers or preservatives. Of course, the composition can be provided in a lyophilized form to prolong storage stability.

In diagnostic use, the binding agent is exploited to detect the presence of cells presenting misfolded FasR. The senescent cells to be detected may be in a sample obtained from any source, including a living subject. A subject includes one who is to be tested, or has been tested for prediction, assessment or diagnosis of a disease or disorder associated with a given misfolded protein target. The subject may have been previously assessed or diagnosed using other methods, such as those in current clinical practice, or may be selected as part of a general population (a control subject). A subject may be a transgenic animal, e.g. a rodent, such as a mouse, that produces a cell presenting misfolded FasR. For example, the subject may be a transgenic mouse overexpressing a normal form of the target protein or may be a wild-type mouse or other rodent that has been infected with a misfolded form of the target protein.

To assist with the identification of subjects who are candidates for treatment with the antibody or vaccine compositions of the invention, the present invention further provides for the detection of an epitope by in vitro or in vivo diagnostic methods.

To detect the presence of a misfolded protein in any given sample, the present invention provides a detection method in which a sample suspected to contain the misfolded protein is treated with an antibody or binding fragment that binds selectively to an epitope presented uniquely by the misfolded protein relative to the natively folded form of that protein; and determining whether an antigen:antibody complex has formed, the formation thereof being indicative of the presence in the sample of a misfolded form of said protein.

In a related embodiment, the labeled antibodies of the invention, or labeled form of a binding fragment thereof, can be used in vivo to image the presence of the misfolded protein to which the antibody binds. To this end, the present invention provides an antibody or fragment in a form coupled to an agent useful for in vivo imaging, such as isotopes of technetium, gadolinium, and the like.

In situ detection of the binding to cancer cells bearing misfolded FasR can also be performed using the present antibody or fragment, by immunofluorescence or immuno-electron microscopy. For this purpose, a histological specimen is removed from the patient, and a labeled form of the present antibody is applied to it, preferably by overlaying the antibody on a biological sample, in keeping with standard immunohistochemistry techniques. This procedure also allows for distribution of the antigen to be examined within biopsied tumour tissue, to reveal only those sites at which the antigen is presented in misfolded form. It will be apparent for those skilled in the art that a wide variety of histological methods are readily available for in situ detection.

More particularly, antibodies or binding fragments of the present invention may be used to monitor the presence or absence of antibody reactivity in a biological sample, e.g., a tissue biopsy from brain, skin, liver, heart, kidney, pancreas, bowel, spleen, muscle, fat, skin, ovary and the like, from a cell, or from fluid such as cerebrospinal fluid, blood including plasma, urine, seminal fluid, and the like, using standard detection assays. Immunological assays may involve direct detection, and are particularly suited for screening large amounts of samples for the presence of senescent cells that present misfolded surface protein. For example, antibodies may be Used in any standard immunoassay format (e.g., ELISA, Western blot, immunoprecipitation, flow cytometry or RIA assay) to measure complex formation. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. For example, using the antibodies described herein, misfolded PrP is readily detected at the cell surface using standard flow cytometry methods. Samples found to contain labeled complex compared to appropriate control samples are taken as indicating the presence of misfolded FasR, and are thus indicative of a disease state amenable to treatment with the present antibodies.

Screening results that are obtained with misfolded protein binding agents can be confirmed using any other test appropriate for cell detection or characterization. It is known, for instance that misfolded FasR is detectable not only on senescent cells, but also on certain cancer cells. In certain instances, therefore, the cell detection method can be accompanied by a test that is confirmatory for the cell type of interest. In embodiments, the test can confirm that the misfolded FasR+ cell is a senescent cells, using the established assay for B-galactosidase activity. It has been shown that senescent cells will use B-galactosidase as a substrate when cultured at mildly acidic pH, such as pH 6.0. As described by Dimri et al in U.S. Pat. No. 5,795,728, incorporated herein by reference, senescent cells can be identified by culturing cells in the presence of a B-galactosidase substrate, such as X-gal, and at pH 6.0. The cultured cells or tissue are then fixed in a solution such as 2% formaldehyde, 0.2% glutaraldehyde and PBS. The appearance of reaction products, revealed by staining, indicates that the cultured cell is senescent. Alternatively, any cell or tissue can be examined for senescence by assaying for the presence of INK4a/ARF expression, as described by Sharpless et al in U.S. Pat. No. 8,158,347, also incorporated herein by reference. An elevation in this expression product indicates the tested cell is senescent. Of course, other methods are useful to identify senescent cells, including measurement of the incorporation of labeled DNA precursors such as 3H-thymidine and BrdU or measurement of cell markers that are expressed only in proliferating cells, such as PCNA or MTT. Senescent cells will test negative for these markers.

Such assays can also be performed prior to administering a binding agent or immunogen described herein and/or to identify subjects to be treated. In an embodiment, the method comprises detecting misfolded FasR+ cells in a sample containing cells to be screened according to a method described herein, for example using a binding agent, B-galactosidease assay etc or combinations thereof; and administering to the subject a binding agent that selectively binds misfolded FasR disease cells in an amount effective to reduce the number of such cells, wherein the biding agent binds selectively to FasR having a misfolded conformation, relative to said protein in a natively folded conformation. In an embodiment, the method comprises detecting senescent cells in a sample containing cells to be screened according to a method described herein, for example using a binding agent, B-galactosidase assay etc or combinations thereof; administering to the subject a binding agent that binds selectively to FasR having a misfolded conformation, for example to treat a subject at risk for a disease associated with aberrant FasR folding or signalling.

When applied in vitro, the detection method entails analysis of a cell-containing sample of body fluid or tissue or organ from a subject, usually a subject suspected of having endogenous misfolded target protein. For example, the biological sample may a body fluid such as cerebrospinal fluid, blood, plasma, lymph fluid, serum, urine or saliva. A tissue or organ sample, such as that obtained from a solid or semi-solid tissue or organ, may be digested, extracted or otherwise rendered to a liquid form—examples of such tissues or organs include cultured cells, blood cells, brain, neurological tissue, skin, liver, heart, kidney, pancreas, islets of Langerhans, bone marrow, blood, blood vessels, heart valve, lung, intestine, bowel, spleen, bladder, penis, face, hand, bone, muscle, fat, cornea or the like, including cancerous forms thereof. A biological sample or samples may be taken from a subject at any appropriate time, including before the subject is diagnosed with, or suspected of having a protein misfolding associated disease or disorder, during a therapeutic regimen for the treatment or amelioration of symptoms of that disease or disorder, after death of the subject (regardless of the cause, or suspected cause). Alternately, a biological sample may include donated body fluid or tissue, such as blood, plasma or platelets when in care of a centralized blood supply organization or institution.

The presence in the sample of a cell presenting misfolded FasR is confirmed if the antibody forms a detectable antigen: antibody complex. The formation of such complex can be determined using a wide variety of protocols that include ELISA, RIA, flow cytometry, Western blots, immunohistochemistry and the like. To reveal the complex and hence the presence of the epitope in the sample, the antibody desirably is provided as a labeled antibody by conjugation or coupling to an agent that is detectable either visually or with the aid of instrumentation. The agent, or label, is capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. Alternatively, the epitope can be revealed using a labeled secondary reagent that binds to the epitope antibody, such as a labeled antibody that binds the epitope antibody, to reveal presence of the epitope indirectly. The presence of an antibody:antigen complex may be detected by indirect means that do not require the two agents to be in solution. For instance, the complex is detectable indirectly using flow cytometry, where the antibody binds to, and forms an antibody:antigen complex with, the epitope presented on the surface of an intact cell. The application of the antibodies for detection of cell-surface forms of the epitope is a very useful embodiment of the invention particularly for detection of senescent cells presenting such epitopes. Detection of such cells can be achieved using the well-established technique of flow cytometry. It will also be appreciated that the antigen:antibody complex can also be identified by non-antibody based methods, that include those which sort proteins based on size, charge and mobility, such as electrophoresis, chromatography, mass spectroscopy and the like.

In a related embodiment, the labeled antibodies of the invention, or labeled form of a binding fragment thereof, can be used in vivo to image the presence of senescent cells that present the misfolded protein to which the antibody binds. To this end, the present invention provides an antibody or fragment in a form coupled to an agent useful for in vivo imaging, such as isotopes of technetium, gadolinium, and the like. In specific embodiments, the antibodies are selected from 3d-19 and 3a-118, and misfolded FasR-binding antibody fragments and conjugates thereof.

In therapeutic use, the agents that bind selectively to a misfolded human FasR can be used to treat patients or subjects presenting with or at risk for a disease associated with aberrant FasR folding or signalling.

For therapeutic use, passive immunotherapy can be adopted by administering binding agents that are antibodies or binding fragments thereof. In the alternative, active immunotherapy can be adopted using vaccines that elicit the production of such antibodies.

For treatment, the active ingredient, such as the immunogen used for active immunization and the antibody used for passive immunization are used in "effective amounts". These are amounts useful, in a treatment regimen, to reduce the effect of the endogenous misfolded FasR+ cells by eliminating or reducing the number of such cells endogenous to the recipient. It will be apparent that the present invention is applicable to a wide variety of diseases, and that the particular amount and treatment regimen effective to reduce the effect of the endogenous protein will vary with each disease, in accordance with established clinical practice for each disease.

Therapeutics according to the invention may be administered with a pharmaceutically acceptable diluent, carrier, or excipient, in unit dosage form.

Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration.

For the treatment of subjects presenting with senescent cells positive for misfolded target protein, the appropriate dosage of agent, e.g., an antibody, fragment or conjugate, will depend on the type of disease to be treated, as defined above, the severity and course of the disease, whether the agent is administered for preventative or therapeutic purposes, previous therapy, the patients clinical history and response to the agent, and the discretion of the attending physician. The agent is suitably administered to the patient at one time or over a series of treatments, in accordance with dosing regimens discussed above.

It is anticipated that the present antibodies, fragments and antibody-toxin conjugates will be useful to deplete of endogenous cells that are misfolded FasR+, thereby to limit the impact of these cells in aberrant signalling. This will be useful particular for the treatment of cancer, and other indications in which impaired FasR signalling is implicated.

It is demonstrated that senescent cells presenting misfolded FasR create a local environment that supports tumorigenesis in neighbouring cells. Treatment by the present method can accordingly be useful to treat solid and liquid cancers in various tissues, including cancers of the blood, lung, prostate, skin, breast, ovary, head and neck, colon, and the like. Such treatment is expected to result in a decrease in the rate of tumour formation directly, and thus indirectly also on the number, size and distribution of responsive cancer cells and tumours.

The invention also includes articles of manufacture as well as kits that comprise components useful to perform the diagnostic and therapeutic methods of the present invention. The articles of manufacture comprise packaging material and a composition comprising an antibody or antisera that is one of the two antibody species herein described. The composition includes a physiologically or pharmaceutically acceptable excipient, and the packaging material may include a label which indicates the active ingredients of the composition (e.g. the antisera or antibody). The label may further include an intended use of the composition, for example as a diagnostic reagent to be used with kits as set out herein.

Also provided is an article of manufacture, comprising packaging material and a composition comprising a peptide, or one or more peptides, having SEQ ID No. 2 or No. 5, or an equivalent thereof that binds one of the two antibodies herein described. The composition may include a physiologically or pharmaceutically acceptable excipient, and the packaging material may include a label which indicates the active ingredients of the composition (e.g. the peptide). The label may further include an intended use of the composition, for example as a therapeutic or prophylactic reagent, or as a composition to induce an immune response in a subject for the purpose of producing antisera or antibodies specific to senescent cell target protein, to be used with kits as set out herein.

In a further embodiment, there is provided a kit comprising a composition comprising one or more peptides as provided herein, along with instructions for use of the compound or composition for the production or screening of antibodies for identification of senescent cells. The kit may be useful for production and/or identification of senescent cell-specific antibodies or antisera, and the instructions may include, for example, dose concentrations, dose intervals, preferred administration methods, methods for immunological screening or testing, or the like.

In another embodiment, a kit for the preparation of a medicament, comprising a composition comprising one or more peptides as provided herein, along with instructions for its use is provided. The instructions may comprise a series of steps for the preparation of the medicament, the medicament being useful for inducing a therapeutic or prophylactic immune response in a subject to whom it is administered. The kit may further comprise instructions for use of the medicament in treatment for treatment, prevention or amelioration of one or more symptoms of a disease or disorder associated with FasR misfolding, or in which protein FasR misfolding is implicated, and include, for example, dose concentrations, dose intervals, preferred administration methods or the like.

In another embodiment, a kit for diagnosing a disease or disorder associated with protein misfolding is provided. The kit comprises one or more misfolded FasR-selective antibodies as described herein, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable colorimetric or chemiluminescent reaction. The kit may further comprise reagents for performing the detection reaction, including enzymes such as proteinase K, blocking buffers, homogenization buffers, extraction buffers, dilution buffers or the like. The kit may further comprise reagents useful to perform the confirmatory B-galactosidase test for senescence, as discussed above.

In another embodiment, a kit for detecting the presence of misfolded FasR+ cells in a biological sample is provided. The kit comprises one or more antibodies or antisera that specifically bind the misfolded protein presented by the senescent cells, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable colorimetric or chemiluminescent reaction. The kit may further comprise reagents for performing the detection reaction, including enzymes such as proteinase K, blocking buffers, homogenization buffers, extraction buffers, dilution buffers or the like. The kit may further comprise reagents useful to perform the confirmatory B-galactosidase test for senescence, as discussed above.

Example 1—Cell Detection, FasR-Based

Fas receptor (FasR) is known also as human tumour necrosis factor superfamily member 6 receptor (hTNFRSM6), and as CD95, and is implicated in cancer. It is a death receptor on the surface of cells that leads to caspase-mediated programmed cell death (apoptosis). Antibodies to a misfolded form of this protein were prepared based on the epitopes predicted by Cashman et al, WO 2010/040209, as shown below:

| Protein | Residues | Sequence | ID No. |
|---|---|---|---|
| Human FASR | 52-60 | LHHDGQFCH | 2 |
| (hTNFR6) | 70-80 | ARDCTVNGDEP | 3 |
| P25445 residues | 105-111 | RLCDEGH | 4 |
| 1-335 | 136-142 | NSTVCEH | 5 |
|  | 167-189 | EEPSRSNLGWLCL | 6 |

To raise antibodies against misfolded FasR, peptides comprising the FasR epitope sequences LHHDGQFCH (SEQ ID No. 2) and NSTVCEH (SEQ ID No. 5) were synthesized using standard methods and then coupled to carrier proteins. Prepared immunogens included both KLH-Cys-X and OVA-Cys-X, where X is NSTVCEH (SEQ ID No: 5) or LHHDGQFCH (SEQ ID No: 2).

New Zealand white rabbits were immunized subcutaneously with 0.4 mg peptide-KLH conjugates in complete Freund's adjuvant. After the initial immunization, animals were boosted several times every 2-3 weeks. The rabbit with the best titer in immunoassay was intravenously boosted with peptide antigen again, four days before the removal of the spleen. The hybridoma fusion was performed using conventional PEG cell fusion methodology. Splenocytes were harvested from the immunized rabbit and fused with rabbit plasmacytoma cells 240E-W2 (U.S. Pat. No. 5,675,063) using PEG4000 (Sigma Chemical, St. Louis, Mo.) and selected by HAT (hypoxanthine, aminopterin, and thymidine). At the end of selection hybridoma supernatants were collected and evaluated in various assays. Selected hybridomas were subsequently subcloned by limited dilution to obtain monoclonal hybridomas.

The antibody heavy and light chain genes for monoclonal AMF-3a-118 and AMF-3d-19 were cloned from the hybridoma cells. Total RNA was extracted and reverse-transcribed to cDNA using the Qiagen TurboCapture mRNA kits. DNA fragments for L chain and the variable region (VH) of H chain of rabbit IgG were amplified by PCR with rabbit H and L chain primers. The L chain fragment was cloned into pTT5 mammalian expression vector and the VH fragment fused in-frame to the constant region of H chain pTT5 Heavy chain vector For each hybridoma clone, three plasmid DNA clones for H and L chains were sequenced and expressed as recombinant RabMAb for characterization.

Plasmids encoding the IgG heavy and light chains of AMF-3a-118 and AMF-3d-19 were isolated from transformed E. coli using EndoFree® plasmid purification kit (Qiagen). Human HEK-293-6E cells were used for transient expression of AMF-3a-118 and AMF-3d-19 antibodies. The antibody plasmids were transfected into cells at logarithmic growth phase using FreeStyle™ MAX Reagent 293 fectin (Invitrogen, Cat: 51-0031) and cultured in FreeStyle™ 293 Expression Medium (Invitrogen, Cat: 12338-18) according to manufacturer's instructions. The antibody secreted into the culture medium was collected by spinning at 7000 rpm for 15 minutes to remove cell debris. The cleared culture supernatant was purified by protein A chromatography (Hi-Trap™ rProtein A FF, GE healthcare, CAT: 17-5080-01) under endotoxin free condition. Antibodies were eluted from the column in citrate elution buffer (SIGMA, CAT: C2404-100G) and adjusted to neutral pH with sodium bicarbonate buffer. The antibody preparations were concentrated and exchanged into PBS buffer.

Purified antibody was filter-sterilized and stored at 4° C. in PBS buffer (pH 7.4). The protein concentration was determined by UV absorption 280 nm) assay and PBS buffer was used a blank buffer. To measure protein purity, SDS-PAGE was performed with Bio-Rad mini electrophoresis system according to the manufacturer's instructions. The gel was then stained with Coomassie brilliant blue. The resolving gel was 12% acrylamide and the stacking gel was 4% acrylamide. The assayed samples showed 2 bands (Heavy chain and Light chain) in reduced SDS-PAGE, and one band (whole IgG molecule) in non-reduced SDS-PAGE.

Thus in a preferred embodiment, the antibody is provided as a preparation that exhibits (a) a concentration of greater than about 1 mg/ml, (b) and migration as a single protein band when measured by non-reducing SDS-PAGE.

Maxisorp 96-well plates were coated overnight at 2-8° C. with 100 ng/well of BSA-peptide in PBS. After blocking with PBST/casein, primary antibodies were added and incubated for 1 hour at room temperature. Rabbit antibodies were detected using goat anti-rabbit IgG-HRP and TMB substrate. After stopping the reaction with 0.25M sulfuric acid, absorbance was measured at 450 nm.

Recombinant Fas extracellular domain-Fc fusion protein (Aragen) was mixed with LDS sample buffer (Life Technologies) and sample reducing agent (Life Technologies) and heated at 80° C. for 20 minutes. After cooling for 15 minutes, Maxisorp 96-well plates were coated with 100 ng/well of denatured Fas and incubated at 2-8° C. overnight. After blocking with PBST/BSA, primary antibodies were added and incubated for 1 hour at room temperature. Remaining steps were as described for anti-peptide ELISAs.

His-tagged Fas (Creative Biomart) was mixed with Talon Dynabeads (Invitrogen) in round-bottom polystyrene 96-well plates for 30 minutes at room temperature. After beads were collected on a magnet, beads were washed 3× with PBST, then mixed with primary antibodies at room temperature for 60 minutes. Bound primary antibodies were detected with goat anti-rabbit IgG-HRP and TMB substrate. Supernatant was transferred to a flat-bottom 96-well plate (Nunc), the reaction stopped with 0.25M sulfuric acid, and absorbance was measured at 450 nm.

Antibodies having particularly good binding profiles include antibody AMF-3a-118 for the peptide LHH-DGQFCH (SEQ ID No: 2), and antibody AMF-3d-19 for the peptide NSTVCEH (SEQ ID No: 5). These antibodies have the full length protein sequences set out in SEQ ID No. 31 (light chain) and SEQ ID No.29 (heavy chain) for 3a-118, and sequences set out in SEQ ID No. 45 (light chain) and SEQ ID No.43 (heavy chain) for 3d-19.

Polynucleotides encoding them have the sequences set out in SEQ ID No. 39 (heavy chain) and SEQ ID No. 41 (light chain) for 3a-118 and SEQ ID No. 53 (heavy chain) and SEQ ID No. 55 (light chain) for antibody 3d-19. The important complementarity determining regions (CDRs) of these antibodies are set out below:

AMF-3a-118

For the heavy chain:

| | |
|---|---|
| CDR1 | (SEQ ID No. 33) |
| CDR2 | (SEQ ID No. 34) |
| CDR3 | (SEQ ID No. 35) |

For the light chain:

| | |
|---|---|
| CDR1 | (SEQ ID No. 36) |
| CDR2 | (SEQ ID No. 37) |
| CDR3 | (SEQ ID No. 38) |

AMF-3d-19

For the heavy chain:

| | |
|---|---|
| CDR1 | (SEQ ID No. 47) |
| CDR2 | (SEQ ID No. 48) |
| CDR3 | (SEQ ID No. 49) |

For the light chain:

| | |
|---|---|
| CDR1 | (SEQ ID No. 50) |
| CDR2 | (SEQ ID No. 51) |
| CDR3 | (SEQ ID No. 52) |

Figure 5:
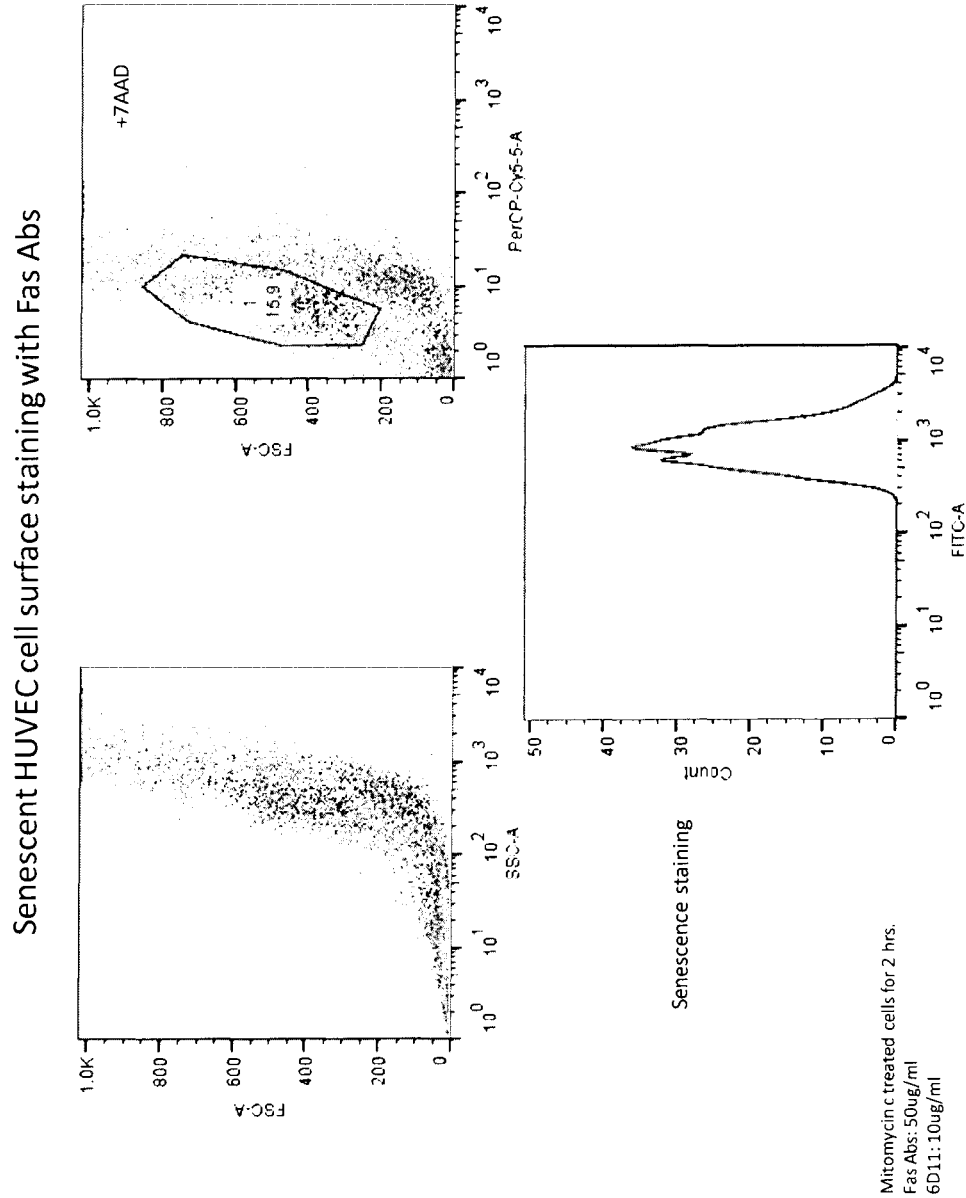
FIG. 5 shows results of flow cytometry for antibodies herein described.

These misfolded FasR antibodies were assessed for their ability to detect senescent cells. More particularly, HUVEC cells were seeded at 50% confluence in 6-well culture plates and cultured in standard growth medium for 24 hours. Media was then removed and the cells were treated with 10 µg/ml Mitomycin C for 2 hrs in fresh cell culture medium. The solution was then removed and the cells were washed twice in PBS for about 30 seconds per wash. Lysosomal alkalinization was induced using the SA-β-gal staining kit, according to the supplier's instructions (Cell Biolabs, CBA-232). The cells were ultimately washed three times in PBS. A cell scraper was used to harvest the cells, and blocking with PBS containing 10% NGS for 30 minutes on ice. Those cells were then stained by first incubating the cells on ice with primary antibodies, i.e., antibodies 3a-118 and 3d-19 at 40 µg/ml and antibody 6D11 as control at 5 µg/ml, washing in cold PBS/2% NGS, and then incubating for 30 minutes on ice with secondary Alexa-488 labeled antibodies. Cells were then subjected to flow cytometry and analyzed. Results are shown in FIG. 5. Thus, adherent tumor cell lines and primary cells were detached from flasks using non-enzymatic cell-dissociation buffer (Invitrogen). Primary cells were frozen in 10% DMSO and thawed on the day of testing. Binding of antibodies to peptide or denatured Fas was performed by ELISA as described above. Antibodies were titrated to provide binding curves. EC50 values were calculated using GraphPad software.

Cells were incubated with primary antibodies for 30 minutes at 2-8° C. Following washing, cells were incubated with goat anti-rabbit AF488 or goat anti-mouse AF488 for 30 minutes at 2-8° C. After the final wash, cells were incubated in 1 µg/mL propidium iodide. Cells were analyzed using either a Becton Dickinson FACSCalibur or a Becton Dickinson FACS Canto II and FCS Express Software (De-Novo Systems).

When treated and untreated cells were incubated with either (1) a standard murine antibody (mIgG), (2) a PrP antibody that binds PrP in both natively and misfolded conformations (6D11), or (3) the FasR antibodies that binds the noted exposed epitopes and thus bind selectively to FasR in a misfolded state, it was revealed that senescent HUVECs were bound selectively by the misfolded FasR antibodies.

In all, about 170 polyclonal hybridoma supernatants against four different Fas DSE peptides were peptide specific and were selected for further evaluation. All 170 hybridoma supernatants were tested for binding to native FasR and denatured FasR by ELISA, and for binding to eight tumor cell lines. Fifteen antibodies were selected for further evaluation. Of these, only the two antibodies (AMF-3a-118 and AMF-3d-19) exhibited the desired characteristics of preferential binding to denatured (misfolded) FasR compared to native FasR (by ELISA) and preferential binding to tumor cells compared to normal cells (by FACS).

All citations are herein incorporated by reference, as if each individual publication was specifically and individually indicated to be incorporated by reference herein and as though it were fully set forth herein.

```
                    Table of Sequences
SEQ
ID      Subject                      Sequence 2       misfolded hFas epitope       LHHIDGQFCH 3       misfolded hFas epitope       ARDCTVNGDEP 4       misfolded hFas epitope       RLCDEGH 5       misfolded hFas epitope       NSTVCEH 6       misfolded hFas epitope       EEPSRSNLGWLCL 29      AMF-3a-118 heavy chain
M E T G L R W L L L V A V L K G V Q C Q
S V E E S G G R L V T P G T P L T L T C
K A S G F S L S D S R V S W V R Q A P G
K G L E W I G I V G I G W N I Y H A N W
```

Table of Sequences

| SEQ ID | Subject | Sequence |
|---|---|---|
| | | A K G R F T I S K T S S T T V D L K I T |
| | | S P T V E D T A T Y F C A R G L G G G T |
| | | V I W G P G T L V T V S L G Q P K A P S |
| | | V F P L A P C C G D T P S S T V T L G C |
| | | L V E G Y L P E P V T V T W N S G T L T |
| | | N G V R T F P S V R Q S S G L Y S L S S |
| | | V V S V T S S S Q P V T C N V A H P A T |
| | | N T K V D K T V A P S T C S K P T C P P |
| | | P E L L G G P S V F I F P P K P K D T L |
| | | M I S R T P E V T C V V V D V S Q D D P |
| | | E V Q F T W Y I N N E Q V R T A R P P L |
| | | R E Q Q F N S T I R V V S T L P I A H Q |
| | | D W L R G K E F K C K V H N K A L P A P |
| | | I E K T I S K A R G Q P L E P K V Y T M |
| | | G P P R E E L S S R S V S L T C M I N G |
| | | F Y P S D I S V E W E K N G K A E D N Y |
| | | K T T P A V L D S D G S Y F L Y S K L S |
| | | V P T S E W Q R G D V F T C S V M H E A |
| | | L H N H Y T Q K S I S R S P G K - |
| 30 | AMF-3a-118 heavy chain variable region | M E T G L R W L L L V A V L K G V Q C Q<br>S V E E S G G R L V T P G T P L T L T C<br>K A S G F S L S D S R V S W V R Q A P G<br>K G L E W I G I V G I G W N I Y H A N W<br>A K G R F T I S K T S S T T V D L K I T<br>S P T V E D T A T Y F C A R G L G G G T<br>V I W G P G T L V T V S L |
| 31 | AMF-3a-118 light chain | M D T R A P T Q L L G L L L L W L P G A<br>T F A Q V L T Q T P A S V S A A V G G T<br>V T I S C Q S S E S V Y K N N Y L S W F<br>Q Q K P G Q P P K L L I Y E A S K L A S<br>G V S T R F K G S G S G T Q F T L T I S<br>G V Q C D D A A T Y Y C L G E F S C Y S<br>G D C G T F G G G T A V V V K G D P V A<br>P T V L I F P P A A D Q V A T G T V T I<br>V C V A N K Y F P D V T V T W E V D G T<br>T Q T T G I E N S K T P Q N S A D C T Y<br>N L S S T L T L T S T Q Y N S H K E Y T<br>C K V T Q G T T S V V Q S F N R G D C - |
| 32 | AMF-3a-118 light chain variable region | M D T R A P T Q L L G L L L L W L P G A<br>T F A Q V L T Q T P A S V S A A V G G T<br>V T I S C Q S S E S V Y K N N Y L S W F<br>Q Q K P G Q P P K L L I Y E A S K L A S<br>G V S T R F K G S G S G T Q F T L T I S<br>G V Q C D D A A T Y Y C L G E F S C Y S<br>G D C G T F G G G T A V V V K |
| 33 | Ab 3a-118 CDR1 heavy | DSRVS |
| 34 | Ab 3a-118 CDR2 heavy | IVGIGWNIYHANWAKG |
| 35 | Ab 3a-118 CDR3 heavy | GLGGGTVI |
| 36 | Ab 3a-118 CDR1 light | QSSESVKNNYLS |
| 37 | Ab 3a-118 CDR2 light | EASKLAS |
| 38 | Ab 3a-118 CDR3 light | LGEFSCYSGDCGT |
| 39 | AMF-3a-118 heavy chain-encoding DNA | ATGGAGACTGGGCTGCGCTGGCTTCTCCTGGTCGCTGTGCTCAAAGGTGT<br>CCAGTGTCAGTCGGTGGAGGAGTCCGGGGGTCGCCTGGTCACGCCTGGG<br>GACACCCTGACACTCACCTGCAAAGCCTCTGGATTCTCCCTCAGTGAC<br>TCTAGAGTGAGCTGGGTCCGCCAGGCTCCAGGGAAGGGGCTGGAATGGA<br>TCGGAATCGTTGGCATTGGTTGGAATATATACCACGCGAACTGGGCGAA<br>AGGCCGATTCACCATCTCCAAAACGTCGTCGACCACGGTGGATTTGAAA<br>ATCACCAGTCCGACAGTCGAGGACACGGCCACCTATTTCTGTGCCAGAG<br>GTCTGGGTGGTGGTACTGTCATCTGGGGCCCAGGCACCCTGGTCACCGT<br>CTCCTTAGGGCAACCTAAGGCTCCATCAGTCTTCCCACTGGCCCCCTGC |
| | | TGCGGGGACACACCCAGCTCCACGGTGACCCTGGGCTGCCTGGTCAAAG<br>GGTACCTCCCGGAGCCAGTGACCGTGACCTGGAACTCGGGCACCCTCAC<br>CAATGGGGTACGCACCTTCCCGTCCGTCCGGCAGTCCTCAGGCCTCTAC<br>TCGCTGAGCAGCGTGGTGAGCGTGACCTCAAGCAGCCAGCCCGTCACCT<br>GCAACGTGGCCCACCCAGCCACCAACACCAAAGTGGACAAGACCGTTGC<br>GCCCTCGACATGCAGCAAGCCCACGTGCCCACCCCCTGAACTCCTGGGG<br>GGACCGTCTGTCTTCATCTTCCCCCCAAAACCCAAGGACACCCTCATGA<br>TCTCACGCACCCCCGAGGTCACATGCGTGGTGGTGGACGTGAGCCAGGA<br>TGACCCCGAGGTGCAGTTCACATGGTACATAAACAACGAGCAGGTGCGC<br>ACCGCCCGGCCGCCGCTACGGGAGCAGCAGTTCAACAGCACGATCCGCG<br>TGGTCAGCACCCTCCCCATCGCGCACCAGGACTGGCTGAGGGGCAAGGA<br>GTTCAAGTGCAAAGTCCACAACAAGGCACTCCCGGCCCCCATCGAGAAA<br>ACCATCTCCAAAGCCAGAGGGCAGCCCCTGGAGCCGAAGGTCTACACCA<br>TGGGCCCTCCCCGGGAGGAGCTGAGCAGCAGGTCGGTCAGCCTGACCTG<br>CATGATCAACGGCTTCTACCCTTCCGACATCTCGGTGGAGTGGGAGAAG<br>AACGGGAAGGCAGAGGACAACTACAAGACCACGCCGGCCGTGCTGGACA<br>GCGACGGCTCCTACTTCCTCTACAGCAAGCTCTCAGTGCCCACAGTGA<br>GTGGCAGCGGGGCGACGTCTTCACCTGCTCCGTGATGCACGAGGCCTTG<br>CACAACCACTACACGCAGAAGTCCATCTCCCGCTCTCCGGGTAAATGA |
| 40 | AMF-3a-118 heavy chain variable region-encoding DNA | ATGGAGACTGGGCTGCGCTGGCTTCTCCTGGTCGCTGTGCTCAAAGGTGT<br>CCAGTGTCAGTCGGTGGAGGAGTCCGGGGGTCGCCTGGTCACGCCTGGGA<br>CACCCTGACACTCACCTGCAAAGCCTCTGGATTCTCCCTCAGTGACTCT<br>AGAGTGAGCTGGGTCCGCCAGGCTCCAGGGAAGGGGCTGGAATGGATCGG<br>AATCGTTGGCATTGTTGGAATATATACCACGCGAACTGGGCGAAAGGCC<br>GATTCACCATCTCCAAAACGTCGTCGACCACGGTGGATTTGAAAATCACC<br>AGTCCGACAGTCGAGGACACGGCCACCTATTTCTGTGCCAGAGGTCTGGG<br>TGGTGGTACTGTCATCTGGGGCCCAGGCACCCTGGTCACCGTCTCCTTA |
| 41 | AMF 3a-118 light chain-encoding DNA | ATGGACACGAGGGCCCCCACTCAGCTGCTGGGGCTCCTGCTGCTCTGGCT<br>CCCAGGTGCCACATTTGCCCAAGTGCTGACCCAGACTCCAGCCTCCGTGT<br>CTGCAGCTGTGGGAGGCACAGTCACCATCAGTTGCCAGTCCAGTGAGAGT<br>GTTTATAAGAACAACTACTTATCCTGGTTTCAGCAGAAACCAGGACAGCC<br>TCCCAAGCTCCTGATCTACGAAGCATCCAAACTGGCATCTGGGGTCTCAA<br>CGCGGTTCAAAGGCAGTGGATCTGGGACACAGTTCACTCTCACCATCAGC<br>GGCGTGCAGTGTGACGATGCTGCCACATACTACTGTCTAGGCGAATTTAG<br>TTGTTATAGTGGTGATTGTGGTACTTTCGGCGGAGGGACCGCGGTGGTGG<br>TCAAAGGTGATCCAGTTGCACCTACTGTCCTCATCTTCCCACCAGCTGCT<br>GATCAGGTGGCAACTGGAACAGTCACCATCGTGTGTGTGGCGAATAAATA<br>CTTTCCCGATGTCACCGTCACCTGGGAGGTGGATGGCACCACCCAAACAA<br>CTGGCATCGAGAACAGTAAAACACCGCAGAATTCTGCAGATTGTACCTAC<br>AACCTCAGCAGCACTCTGACACTGACCAGCACACAGTACAACAGCCACAA<br>AGAGTACACCTGCAAGGTGACCCAGGGCACGACCTCAGTCGTCCAGAGCT<br>TCAATAGGGGTGACTGTTAG |
| 42 | AMF 3a-118 light chain variable region-encoding DNA | ATGGACACGAGGGCCCCCACTCAGCTGCTGGGGCTCCTGCTGCTCTGGCT<br>CCCAGGTGCCACATTTGCCCAAGTGCTGACCCAGACTCCAGCCTCCGTGT<br>CTGCAGCTGTGGGAGGCACAGTCACCATCAGTTGCCAGTCCAGTGAGAGT<br>GTTTATAAGAACAACTACTTATCCTGGTTTCAGCAGAAACCAGGACAGCC<br>TCCCAAGCTCCTGATCTACGAAGCATCCAAACTGGCATCTGGGGTCTCAA<br>CGCGGTTCAAAGGCAGTGGATCTGGGACACAGTTCACTCTCACCATCAGC<br>GGCGTGCAGTGTGACGATGCTGCCACATACTACTGTCTAGGCGAATTTAG<br>TTGTTATAGTGGTGATTGTGGTACTTTCGGCGGAGGGACCGCGGTGGTGG<br>TCAAA |
| 43 | AMF 3d-19 heavy chain | M E T G L R W L L L V A V L K G V Q C Q<br>S L E E S G G R L V T P G T P L T L T C<br>T V S G F S L S R N A I N W V R Q A P G<br>K G L E Y I G I I G S S G V T Y Y A S W<br>A K G R F T I S R T S T T V D L K I T S<br>P T T E D T A T Y F C A R N L Y T G G S<br>N D N L W G P G T L V T V S S G Q P K A<br>P S V F P L A P C C G D T P S S T V T L<br>G C L V K G Y L P E P V T V T W N S G T<br>L T N G V R T F P S V R Q S S G L Y S L<br>S S V V S V T S S S Q P V T C N V A H P<br>A T N T K V D K T V A P S T C S K P T C<br>P P P E L L G G P S V F I F P P K P K D |

Table of Sequences

| SEQ ID | Subject | Sequence |
|---|---|---|
| | | T L M I S R T P E V I C V V V D V S Q D |
| | | D P E V Q F T W Y I N N E Q V R T A R P |
| | | P L R E Q Q F N S T I R V V S T L P I A |
| | | E Q D W L R G R E F K C K V H N E A L P |
| | | A P I E K T I S K A R G Q P L E P K V Y |
| | | T M G P P R E E L S S R S V S L T C M I |
| | | N G F Y P S D I S V E W E K N G K A E D |
| | | N Y K T T P A V L D S D G S Y F L Y S K |
| | | L S V P T S E W Q R G D V F T C S V M H |
| | | E A L H N H Y T Q K S I S R S P G K - |
| 44 | AMF 3d-19 heavy chain variable region | M E T G L R W L L L V A V L K G V Q C Q S L E E S G G R L V T P G T P L T L T C T V S G F S L S R N A I N W V R Q A P G K G L E Y I G I I G S S G V T Y Y A S W A K G R F T I S R I S T T V D L K I T S P T T E D T A T Y F C A R N L Y T G G S N D N L W G P G T L V T V S S |
| 45 | AMF 3d-19 light chain | M D T R V P T Q L L G L L L L W L P G A T F A Q V L T Q T P S P V S A A V G G T V T I N C Q A S K S V Y N N V Q L S W F Q Q K P G Q P P K R L T Y Y A S T L A S G V P S R F K G S G S G T Q F T L T I S D V Q C D D V A T Y Y C A G G Y S S S S D N A F G G G T E V V V K G D P V A P T V L I F P P A A D V Q V A T G T V T I V C V A N K Y F P D V T V T W E V D G T T Q T T G I E N S K T P Q N S A D C T Y N L S S T L T L T S T Q Y N S H K E Y T C K V T Q G T T S V V Q S F N R G D C - |
| 46 | AMF 3d-19 light chain variable region | M D T R V P T Q L L G L L L L W L P G A T F A Q V L T Q T P S P V S A A V G G T V T I N C Q A S K S V Y N N V Q L S W F Q Q K P G Q P P K R L I Y Y A S T L A S G V P S R F K G S G S G T Q F T L T I S D V Q C D D V A T Y Y C A G G Y S S S S D N A F G G G T E V V V K |
| 47 | Ab 3d-19 CDR1 heavy | RNAIN |
| 48 | Ab 3d-19 CDR2 heavy | IIGSSGVTYYASWAKG |
| 49 | Ab 3d-19 CDR3 heavy | NLYTGGSNDNL |
| 50 | Ab 3d-19 CDR1 light | QASKSVYNNVQLS |
| 51 | Ab 3d-19 CDR2 light | YASTLAS |
| 52 | Ab 3d-19 CDR3 light | AGGYSSSSDNA |
| 53 | AMF 3d-19 heavy chain-encoding DNA | ATGGAGACTGGGCTGCGCTGGCTTCTCCTGGTCGCTGTGCTCAAAGGTGT CCAGTGTCAGTCGTTGGAGGAGTCCGGGGGTCGCCTGGTCACGCCTGGGA CACCCCTGACACTCACCTGCACCGTCTCTGGATTCTCCCTCAGTCGCAAT GCAATAAACTGGGTCCGCCAGGCTCCAGGGAAGGGGCTGGAATACATCGG AATCATTGGTAGTAGTGGTGTCACATACTACGCGAGCTGGGCAAAAGGCC GATTCACCATCTCCAGAACCTCGACCACGGTGGATCTGAAAATCACCAGT CCGACAACCGAGGACACGGCCACCTATTTTTGTGCCAGAAATCTTTATAC TGGTGGTAGTAATGATAACTTGTGGGGCCCAGGCACCCTGGTCACCGTCT CCTCAGGGCAACCTAAGGCTCCATCAGTGTTCCCACTGGCCCGCTGCTGC GGGGACACACCCAGCTCCACGGTGACCCTGGGCTGCCTGGTCAAAGGTA CCTCCCGGAGCCAGTGACCGTGAGCTGGAACTCGGGCACGCTCACCAATG GGGTACGCACCTTCCCGTCCGTCCGGCAGTCCTCAGGCCTCTACTCGCTG AGCAGCGTGGTGAGCGTGACCTCAAGCAGCCAGCCCGTCACCTGCAACGT GGCCCACCCAGCCACCAACACCAAAGTGGACAAGACCGTTGCGCCCTCGA CATGCAGCAAGCCCACGTGCCCACCCCCTGAACTCCTGGGGGACCGTCT GTCTTCATCTTCCCCCCAAAACCCAAGGACACCCTCATGATCTCACGCAC CCCCGAGGTCACATGCGTGGTGGTGGACGTGAGCCAGGATGACCCCGAGG TGCAGTTCACATGGTACATAAACAACGAGCAGGTGCGCACCGCCCGGCCG |
| 54 | AMF 3d-19 heavy chain variable region-encoding DNA | ATGGAGACTGGGCTGCGCTGGCTTCTCCTGGTCGCTGTGCTCAAAGGTGT CCAGTGTCAGTCGTTGGAGGAGTCCGGGGGTCGCCTGGTCACGCCTGGGA CACCCCTGACACTCACCTGCACCGTCTCTGGATTCTCCCTCAGTCGCAAT GCAATAAACTGGGTCCGCCAGGCTCCAGGGAAGGGGCTGGAATACATCGG AATCATTGGTAGTAGTGGTGTCACATACTACGCGAGCTGGGCAAAAGGCC GATTCACCATCTCCAGAACCTCGACCACGGTGGATCTGAAAATCACCAGT CCGACAACCGAGGACACGGCCACCTATTTTTGTGCCAGAAATCTTTATAC TGGTGGTAGTAATGATAACTTGTGGGGCCCAGGCACCCTGGTCACCGTCT CCTCA |
| 55 | AMF 3d-19 light chain-encoding DNA | ATGGAGACTGGGCTGCGCTGGCTTCTCCTGGTCGCTGTGCTCAAAGGTGT CCAGTGTCAGTCGGTGGAGGAGTCCGGGGGTCGCCTGGTCACGCCTGGGA CACCCCTGACACTCACCTGCAAAGCCTCTGGATTCTCCCTCAGTGACTCT AGAGTGAGCTGGGTCCGCCAGGCTCCAGGGAAGGGGCTGGAATGGATCGG AATCGTTGGCATTGTTGGAATATATACCACGCGAACTGGGCGAAAGGCC GATTCACCATCTCCAAAACGTCGTCGACCACGGTGGATTTGAAAATCACC ACTCCGACAGTCGAGGACACGGCCACCTATTTCTGTGCCAGAGGTCTCCC TGGTGGTACTGTCATCTGGGGCCCAGGCACCCTGGTCACCGTCTCCTTAG GGCAACCTAAGGCTCCATCAGTCTTCCCACTGGCCCCTGCTGCGGGGAC ACACCCAGCTCCACGGTGACCCTGGGCTGCCTGGTCAAAGGTACCTCCC GGAGCCAGTGACCGTGACCTGGAACTCGGGCACCCTCACCAATGGGGTAC GCACCTTCCCGTCCGTCCGGCAGTCCTCAGGCCTCTACTCGCTGAGCAGC GTGGTGAGCGTGACCTCAAGCAGCCAGCCCGTCACCTGCAACGTGGCCCA CCCAGCCACCAACACCAAAGTGGACAAGACCGTTGCGCCCTCGACATGCA GCAAGCCCACGTGCCCACCCCCTGAACTCCTGGGGGACCGTCTGTCTTC ATCTTCCCCCCAAAACCCAAGGACACCCTCATGATCTCACGCACCCCCGA GGTCACATGCGTGGTGGTGGACGTGAGCCAGGATGACCCCGAGGTGCAGT TCACATGGTACATAAACAACGAGCAGGTGCGCACCGCCCGGCCGCCGCTA CGGGAGCAGCAGTTCAACAGCACGATCCGCGTGGTCAGCACCCTCCCCAT CGCGCACCAGGACTGGCTGAGGGGCAAGGAGTTCAAGTGCAAAGTCCACA ACAAGGCACTCCCGGCCCCATCGAGAAAACCATCTCCAAAGCCAGAGGG CAGCCCCTGGAGCCGAAGGTCTACACCATGGGCCCTCCCCGGGAGGAGCT GAGCAGCAGGTCGGTCAGCCTGACCTGCATGATCAACGGCTTCTACCCTT CCGACATCTCGGTGGAGTGGGAGAAGAACGGGAAGGCAGAGGACAACTAC AAGACCACGCCGGCCGTGCTGGACAGCGACGGCTCCTACTTCCTCTACAG CAAGCTCTCAGTGCCCACGAGTGAGTGGCAGCGGGGCGACGTCTTCACCT GCTCCGTGATGCACGAGGCCTTGCACAACCACTACACGCAGAAGTCCATC TCCCGCTCTCCGGGTAAATGA |
| 56 | AMF 3d-19 light chain variable region-encoding DNA | ATGGAGACTGGGCTGCGCTGGCTTCTCCTGGTCGCTGTGCTCAAAGGTGT CCAGTGTCAGTCGGTGGAGGAGTCCGGGGGTCGCCTGGTCACGCCTGGGA CACCCCTGACACTCACCTGCAAAGCCTCTGGATTCTCCCTCAGTGACTCT AGAGTGAGCTGGGTCCGCCAGGCTCCAGGGAAGGGGCTGGAATGGATCGG AATCGTTGGCATTGTTGGAATATATACCACGCGAACTGGGCGAAAGGCC GATTCACCATCTCCAAAACGTCGTCGACCACGGTGGATTTGAAAATCACC AGTCCGACAGTCGAGGACACGGCCACCTATTTCTGTGCCAGAGGTCTGGG TGGTGGTACTGTCATCTGGGGCCCAGGCACCCTGGTCACCGTCTCCTTA |
| 58 | AMF-3a-118 heavy chain-encoding DNA (vector sequence before and after start codon) | <u>AAGCTT</u>GTACCCTTCACC ATGGAGACTGGGCTGCGCTGGCTTCTCCTGGTCGCTGTGCTCAAAGGTGT CCAGTGTCAGTCGGTGGAGGAGTCCGGGGGTCGCCTGGTCACGCCTGGGA CACCCCTGACACTCACCTGCAAAGCCTCTGGATTCTCCCTCAGTGACTCT AGAGTGAGCTGGGTCCGCCAGGCTCCAGGGAAGGGGCTGGAATGGATCGG AATCGTTGGCATTGTTGGAATATATACCACGCGAACTGGGCGAAAGGCC GATTCACCATCTCCAAAACGTCGTCGACCACGGTGGATTTGAAAATCACC AGTCCGACAGTCGAGGACACGGCCACCTATTTCTGTGCCAGAGGTCTGGG |

Table of Sequences

| SEQ ID | Subject | Sequence |
|---|---|---|

TGGTGGTACTGTCATCTGGGGCCCAGGCACCCTGGTCACCGTCTCCTTAG
GGCAACCTAAGGCTCCATCAGTCTTCCCACTGGCCCCCTGCTGCGGGAC
ACACCCAGCTCCACGGTGACCCTGGGCTGCCTGGTCAAAGGGTACCTCCC
GGAGCCAGTGACCCIGACCTGGAACTCGCGCACCCICACCAATGGGGTAC
GCACCTTCCCGTCCGTCCGGCAGTCCTCAGGCCTCTACTCGCTGAGCAGC
GTGGTGAGCGTGACCTCAAGCAGCCAGCCCGTCACCTGCAACGTGGCCCA
CCCAGCCACCAACACCAAAGTGGACAAGACCGTTGCGCCCTCGACATGCA
GCAAGCCCACGTGCCCACCCCCTGAACTCCTGGGGGGACCGTCTGTCTTC
ATCTTCCCCCCAAAACCCAAGGACACCCTCATGATCTCACGCACCCCCGA
GGTCACATGCGTGGTGGTGGACGTGAGCCAGGATGACCCCGAGGTGCAGT
TCACATGGTACATAAACAACGAGCAGGTGCGCACCGCCCGGCCGCCGCTA
CGGGAGCAGCAGTTCAACAGCACGATCCGCGTGGTCAGCACCCTCCCCAT
CGCGCACCAGGACTGGCTGAGGGGCAAGGAGTTCAAGTGCAAAGTCCACA
ACAAGGCACTCCCGGCCCCCATCGAGAAAACCATCTCCAAAGCCAGAGGG
CAGCCCCTGGAGCCGAAGGTCTACACCATGGGCCCTCCCCGGGAGGAGCT
GAGCAGCAGGTCGGTCAGCCTGACCTGCATGATCAACGGCTTCTACCCTT
CCGACATCTCGGTGGAGTGGGAGAAGAACGGGAAGGCAGAGGACAACTAC
AAGACCACGCCGGCCGTGCTGGACAGCGACGGCTCCTACTTCCTCTACAG
CAAGCTCTCAGTGCCCACGAGTGAGTGGCAGCGGGGCGACGTCTTCACCT
GCTCCGTGATGCACGAGGCCTTGCACAACCACTACACGCAGAAGTCCATC
TCCCGCTCTCCGGGTAAATGAGCGCTGTGCCGGCGAGCT*GCGGCCGC*

59  AMF 3a-118 light chain-encoding DNA (vector sequence before and after start codon)
*aagctt*gtacccttcacc
ATGGACACGAGGGCCCCCACTCAGCTGCTGGGGCTCCTGCTGCTCTGGCT
CCCAGGTGCCACATTTGCCCAAGTGCTGACCCAGACTCCAGCCTCCGTGT
CTGCAGCTGTGGGAGGCACAGTCACCATCAGTTGCCAGTCCAGTGAGAGT
GTTTATAAGAACAACTATTATCTGGTTTCAGCAGAAACCAGGGCAGTCTC
CCCAAGCTCCTGATCTACGAAGCATCCAAACTGGCATCTGGGGTCTCAA
CGCGGTTCAAAGGCAGTGGATCTGGGACAGTTCACTCTCACCATCAGC
GGCGTGCAGTGTGACGATGCTGCCACATACTACTGTCTAGGCGAATTTAG
TTGTTATAGTGGTGATTGTGGTACTTTCGGCGGAGGGACCGCGGTGGTGG
TCAAAGGTGATCCAGTTGCACCTACTGTCCTCATCTTTCCCACCAGCTGCT
GATCAGGTGGCAACTGGAACAGTCACCATCGTGTGTGTGGCGAATAAATA
CTTTTCCCGATGTCACCGTCACCTGGGAGGTGGATGGCACCACCCAAACAA
CTGGCATCGAGAACAGTAAAACACCGCAGAATTCTGCAGATTGTACCTAC
AACCTCAGCAGCACTCTGACACTGACCAGCCACACAGTACAACAGCCACAA
AGAGTACACCTGCAAGGTGACCCAGGGCACGACCTCAGTCGTCCAGAGCT
TCAATAGGGGTGACTGTTAGagtgaga*gcggccgc*

60  AMF 3d-19 heavy chain-encoding DNA (vector sequence before and after start codon)
*aagctt*gtacccttcacc
ATGGAGACTGGGCTGCGCTGGCTTCTCCTGGTCGCTGTGCTCAAAGGTGT
CCAGTGTCAGTCGTTGGAGGAGTCCGGGGGTCGCCTGGTCACGCCTGGGA
CACCCCTGACACTCACCTGCACCGTCTCTGGATTCTCCCTCAGTCGCAAT
GCAATAAACTGGGTCCGCCAGGCTCCAGGGAAGGGGCTGGAATACATCGG
AATCATTGGTAGTAGTGGTGTCACATACTACGCGAGCTGGGCAAAAGGCC
GATTCACCATCTCCAGAACCTCGACCACGGTGGATCTGAAAATCACCAGT
CCGACAACCGAGGACACGGCCACCTATTTTTGTGCCAGAAATCTTTATAC
TGGTGGTAGTAATGATAACTTGTGGGGCCCAGGCACCCTGGTCACCGTCT
CCTCAGGGCAACCTAAGGCTCCATCAGTCTTCCCACTGGCCCCCTGCTGC GGGGACACACCCAGCTCCACGGTGACCCTGGGCTGCCTGGTCAAAGGGTA
CCTCCCGGAGCCAGTGACCGTGACCTGGAACTCGGGCACCCTCACCAATG
GGGTACGCACCTTCCCGTCCGTCCGGCAGTCCTCAGGCCTCTACTCGCTG
AGCAGCGTGGTGAGCGTGACCTCAAGCAGCCAGCCCGTCACCTGCAACGT
GGCCCACCCAGCCACCAACACCAAAGTGGACAAGACCGTTGCGCCCTCGA
CATGCAGCAAGCCCACGTGCCCACCCCCTGAACTCCTGGGGGGACCGTCT
GTCTTCATCTTCCCCCCAAAACCCAAGGACACCCTCATGATCTCACGCAC
CCCCGAGGTCACATGCGTGGTGGTGGACGTGAGCCAGGATGACCCCGAGG
TGCAGTTCACATGGTACATAAACAACGAGCAGGTGCGCACCGCCCGGCCG
CCGCTACGGGAGCAGCAGTTCAACAGCACGATCCGCGTGGTCAGCACCCT
CCCCATCGCGCACCAGGACTGGCTGAGGGGCAAGGAGTTCAAGTGCAAAG
TCCACAACAAGGCACTCCCGGCCCCCATCGAGAAAACCATCTCCAAAGCC
AGAGGGCAGCCCCTGGAGCCGAAGGTCTACACCATGGGCCCTCCCCGGGA
GGAGCTGAGCAGCAGGTCGGTCAGCCTGACCTGCATGATCAACGGCTTCT
ACCCTTCCGACATCTCGGTGGAGTGGGAGAAGAACGGGAAGGCAGAGGAC
AACTACAAGACCACGCCGGCCGTGCTGGACAGCGACGGCTCCTACTTCCT
CTACAGCAAGCTCTCTCAGTGCCCACGAGTGAGTGGCAGCGGGGCGACGTCT
TCACCTGCTCCGTGATGCACGAGGCCTTGCACAACCACTACACGCAGAAG
TCCATCTCCCGCTCTCCGGGTAAATGAGcgctgtgccggcgagct*gcggc cgc*

61  AMF 3d-19 light chain-encoding DNA (vector sequence before and after start codon)
*aagctt*gtacccttcacc
ATGGAGACTGGGCTGCGCTGGCTTCTCCTGGTCGCTGTGCTCAAAGGTGT
CCAGTGTCAGTCGGTGGAGGAGTCCGGGGGTCGCCTGGTCACGCCTGGGA
CACCCCTGACACTCACCTGCAAAGCCTCTGGATTCTCCCTCAGTGACTCT
AGAGTGAGCTGGGTCCGCCAGGCTCCAGGGAAGGGGCTGGAATGGATCGG
AATCTGCATTGGTTGGAATAGATATACCACGCGAACTGGGCGAAAGGCC
GATTCACCATCTCCAAAACGTCGTCGACCACGGTGGATTTGAAAATCACC
AGTCCGACAGTCGAGGACACGGCCACCTATTTCTGTGCCAGAGGTCTGGG
TGGTGGTACTGTCATCTGGGGCCCAGGCACCCTGGTCACCGTCTCCTTAG
GGCAACCTAAGGCTCCATCAGTCTTCCCACTGGCCCCCTGCTGCGGGGAC
ACACCCAGCTCCACGGTGACCCTGGGCTGCCTGGTCAAAGGGTACCTCCC
GGAGCCAGTGACCGTGACCTGGAACTCGGGCACCCTCACCAATGGGGTAC
GCACCTTCCCGTCCGTCCGGCAGTCCTCAGGCCTCTACTCGCTGAGCAGC
GTGGTGAGCGTGACCTCAAGCAGCCAGCCCGTCACCTGCAACGTGGCCCA
CCCAGCCACCAACACCAAAGTGGACAAGACCGTTGCGCCCTCGACATGCA
GCAAGCCCACGTGCCCACCCCCTGAACTCCTGGGGGGACCGTCTGTCTTC
ATCTTCCCCCCAAAACCCAAGGACACCCTCATGATCTCACGCACCCCCGA
GGTCACATGCGTGGTGGTGGACGTGAGCCAGGATGACCCCGAGGTGCAGT
TCACATGGTACATAAACAACGAGCAGGTGCGCACCGCCCGGCCGCCGCTA
CGGGAGCAGCAGTTCAACAGCACGATCCGCGTGGTCAGCACCCTCCCCAT
CGCGCACCAGGACTGGCTGAGGGGCAAGGAGTTCAAGTGCAAAGTCCACA
ACAAGGCACTCCCGGCCCCCATCGAGAAAACCATCTCCAAAGCCAGAGGG
CAGCCCCTGGAGCCGAAGGTCTACACCATGGGCCCTCCCCGGGAGGAGCG
GAGCAGCAGGTCGCTCAGCCTGACCTGCATCATCAACGGCTTCTACCCTT
CCCACATCTCGCTCGAGTGGGAGAAGAACGGGAAGGCAGAGGACAACTAC
AAGACCACGCCGGCCGTGCTGGACAGCGACGGCTCCTACTTCCTCTACAG
CAAGCTCTCAGTGCCCACGAGTGAGTGGCAGCGGGGCGACGTCTTCACCT
GCTCCGTGATGCACGAGGCCTTGCACAACCACTACACGCAGAAGTCCATC
TCCCGCTCTCCGGGTAAATGAgcgctgtgccggcgagct*gcggccgc*

---

SEQUENCE LISTING

<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: linker

<400> SEQUENCE: 1

Ser Gly Gly Gly Gly
1               5

```
<210> SEQ ID NO 2
<211> LENGTH: 9
<212> TYPE: PRT
<213> ORGANISM: Homo Sapiens

<400> SEQUENCE: 2

Leu His His Asp Gly Gln Phe Cys His
1               5

<210> SEQ ID NO 3
<211> LENGTH: 11
<212> TYPE: PRT
<213> ORGANISM: Homo Sapiens

<400> SEQUENCE: 3

Ala Arg Asp Cys Thr Val Asn Gly Asp Glu Pro
1               5                   10

<210> SEQ ID NO 4
<211> LENGTH: 7
<212> TYPE: PRT
<213> ORGANISM: Homo Sapiens

<400> SEQUENCE: 4

Arg Leu Cys Asp Glu Gly His
1               5

<210> SEQ ID NO 5
<211> LENGTH: 7
<212> TYPE: PRT
<213> ORGANISM: Homo Sapiens

<400> SEQUENCE: 5

Asn Ser Thr Val Cys Glu His
1               5

<210> SEQ ID NO 6
<211> LENGTH: 13
<212> TYPE: PRT
<213> ORGANISM: Homo Sapiens

<400> SEQUENCE: 6

Glu Glu Pro Ser Arg Ser Asn Leu Gly Trp Leu Cys Leu
1               5                   10

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10
```

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 456
<212> TYPE: PRT
<213> ORGANISM: Oryctolagus cuniculus

<400> SEQUENCE: 29

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Lys Ala Ser Gly Phe Ser Leu Ser
        35                  40                  45

Asp Ser Arg Val Ser Trp Val Arg Gln Ala Pro Gly Lys Gly Leu Glu
    50                  55                  60

Trp Ile Gly Ile Val Gly Ile Gly Trp Asn Ile Tyr His Ala Asn Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Val Glu Asp Thr Ala Thr Tyr Phe Cys
            100                 105                 110
```

```
Ala Arg Gly Leu Gly Gly Thr Val Ile Trp Gly Pro Gly Thr Leu
        115                 120                 125
Val Thr Val Ser Leu Gly Gln Pro Lys Ala Pro Ser Val Phe Pro Leu
130                 135                 140
Ala Pro Cys Cys Gly Asp Thr Pro Ser Ser Thr Val Thr Leu Gly Cys
145                 150                 155                 160
Leu Val Lys Gly Tyr Leu Pro Glu Pro Val Thr Val Thr Trp Asn Ser
                165                 170                 175
Gly Thr Leu Thr Asn Gly Val Arg Thr Phe Pro Ser Val Arg Gln Ser
            180                 185                 190
Ser Gly Leu Tyr Ser Leu Ser Ser Val Val Ser Val Thr Ser Ser Ser
        195                 200                 205
Gln Pro Val Thr Cys Asn Val Ala His Pro Ala Thr Asn Thr Lys Val
    210                 215                 220
Asp Lys Thr Val Ala Pro Ser Thr Cys Ser Lys Pro Thr Cys Pro Pro
225                 230                 235                 240
Pro Glu Leu Leu Gly Gly Pro Ser Val Phe Ile Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Asp Asp Pro Glu Val Gln Phe Thr Trp Tyr Ile
        275                 280                 285
Asn Asn Glu Gln Val Arg Thr Ala Arg Pro Pro Leu Arg Glu Gln Gln
    290                 295                 300
Phe Asn Ser Thr Ile Arg Val Val Ser Thr Leu Pro Ile Ala His Gln
305                 310                 315                 320
Asp Trp Leu Arg Gly Lys Glu Phe Lys Cys Lys Val His Asn Lys Ala
                325                 330                 335
Leu Pro Ala Pro Ile Glu Lys Thr Ile Ser Lys Ala Arg Gly Gln Pro
            340                 345                 350
Leu Glu Pro Lys Val Tyr Thr Met Gly Pro Pro Arg Glu Glu Leu Ser
        355                 360                 365
Ser Arg Ser Val Ser Leu Thr Cys Met Ile Asn Gly Phe Tyr Pro Ser
    370                 375                 380
Asp Ile Ser Val Glu Trp Glu Lys Asn Gly Lys Ala Glu Asp Asn Tyr
385                 390                 395                 400
Lys Thr Thr Pro Ala Val Leu Asp Ser Asp Gly Ser Tyr Phe Leu Tyr
                405                 410                 415
Ser Lys Leu Ser Val Pro Thr Ser Glu Trp Gln Arg Gly Asp Val Phe
            420                 425                 430
Thr Cys Ser Val Met His Glu Ala Leu His Asn His Tyr Thr Gln Lys
        435                 440                 445
Ser Ile Ser Arg Ser Pro Gly Lys
    450                 455

<210> SEQ ID NO 30
<211> LENGTH: 133
<212> TYPE: PRT
<213> ORGANISM: Oryctolagus cuniculus

<400> SEQUENCE: 30

Met Glu Thr Gly Leu Arg Trp Leu Leu Leu Val Ala Val Leu Lys Gly
1               5                   10                  15
Val Gln Cys Gln Ser Val Glu Glu Ser Gly Gly Arg Leu Val Thr Pro
            20                  25                  30
```

Gly Thr Pro Leu Thr Leu Thr Cys Lys Ala Ser Gly Phe Ser Leu Ser
            35                  40                  45

Asp Ser Arg Val Ser Trp Val Arg Gln Ala Pro Lys Gly Leu Glu
 50                  55                  60

Trp Ile Gly Ile Val Gly Ile Gly Trp Asn Ile Tyr His Ala Asn Trp
 65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Val Glu Asp Thr Ala Thr Tyr Phe Cys
                100                 105                 110

Ala Arg Gly Leu Gly Gly Gly Thr Val Ile Trp Gly Pro Gly Thr Leu
                115                 120                 125

Val Thr Val Ser Leu
                130

<210> SEQ ID NO 31
<211> LENGTH: 239
<212> TYPE: PRT
<213> ORGANISM: Oryctolagus cuniculus

<400> SEQUENCE: 31

Met Asp Thr Arg Ala Pro Thr Gln Leu Leu Gly Leu Leu Leu Leu Trp
 1               5                  10                  15

Leu Pro Gly Ala Thr Phe Ala Gln Val Leu Thr Gln Thr Pro Ala Ser
                20                  25                  30

Val Ser Ala Ala Val Gly Gly Thr Val Thr Ile Ser Cys Gln Ser Ser
                35                  40                  45

Glu Ser Val Tyr Lys Asn Asn Tyr Leu Ser Trp Phe Gln Gln Lys Pro
 50                  55                  60

Gly Gln Pro Pro Lys Leu Leu Ile Tyr Glu Ala Ser Lys Leu Ala Ser
 65                  70                  75                  80

Gly Val Ser Thr Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
                100                 105                 110

Leu Gly Glu Phe Ser Cys Tyr Ser Gly Asp Cys Gly Thr Phe Gly Gly
                115                 120                 125

Gly Thr Ala Val Val Val Lys Gly Asp Pro Val Ala Pro Thr Val Leu
                130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
                195                 200                 205

Thr Ser Thr Gln Tyr Asn Ser His Lys Glu Tyr Thr Cys Lys Val Thr
                210                 215                 220

Gln Gly Thr Thr Ser Val Val Gln Ser Phe Asn Arg Gly Asp Cys
225                 230                 235

<210> SEQ ID NO 32
<211> LENGTH: 135
<212> TYPE: PRT

<213> ORGANISM: Oryctolagus cuniculus

<400> SEQUENCE: 32

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Ser Cys Gln Ser Ser
        35                  40                  45

Glu Ser Val Tyr Lys Asn Asn Tyr Leu Ser Trp Phe Gln Gln Lys Pro
    50                  55                  60

Gly Gln Pro Pro Lys Leu Leu Ile Tyr Glu Ala Ser Lys Leu Ala Ser
65                  70                  75                  80

Gly Val Ser Thr Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Glu Phe Ser Cys Tyr Ser Gly Asp Cys Gly Thr Phe Gly Gly
        115                 120                 125

Gly Thr Ala Val Val Val Lys
    130                 135

<210> SEQ ID NO 33
<211> LENGTH: 5
<212> TYPE: PRT
<213> ORGANISM: Oryctolagus cuniculus

<400> SEQUENCE: 33

Asp Ser Arg Val Ser
1               5

<210> SEQ ID NO 34
<211> LENGTH: 16
<212> TYPE: PRT
<213> ORGANISM: Oryctolagus cuniculus

<400> SEQUENCE: 34

Ile Val Gly Ile Gly Trp Asn Ile Tyr His Ala Asn Trp Ala Lys Gly
1               5                   10                  15

<210> SEQ ID NO 35
<211> LENGTH: 8
<212> TYPE: PRT
<213> ORGANISM: Oryctolagus cuniculus

<400> SEQUENCE: 35

Gly Leu Gly Gly Gly Thr Val Ile
1               5

<210> SEQ ID NO 36
<211> LENGTH: 12
<212> TYPE: PRT
<213> ORGANISM: Oryctolagus cuniculus

<400> SEQUENCE: 36

Gln Ser Ser Glu Ser Val Lys Asn Asn Tyr Leu Ser
1               5                   10

<210> SEQ ID NO 37
<211> LENGTH: 7
<212> TYPE: PRT

<213> ORGANISM: Oryctolagus cuniculus

<400> SEQUENCE: 37

Glu Ala Ser Lys Leu Ala Ser
1               5

<210> SEQ ID NO 38
<211> LENGTH: 13
<212> TYPE: PRT
<213> ORGANISM: Oryctolagus cuniculus

<400> SEQUENCE: 38

Leu Gly Glu Phe Ser Cys Tyr Ser Gly Asp Cys Gly Thr
1               5                   10

<210> SEQ ID NO 39
<211> LENGTH: 1371
<212> TYPE: DNA
<213> ORGANISM: Oryctolagus cuniculus

<400> SEQUENCE: 39

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | caccctgac | actcacctgc | 120 |
| aaagcctctg | gattctccct | cagtgactct | agagtgagct | gggtccgcca | ggctccaggg | 180 |
| aaggggctgg | aatggatcgg | aatcgttggc | attggttgga | atatatacca | cgcgaactgg | 240 |
| gcgaaaggcc | gattcaccat | ctccaaaacg | tcgtcgacca | cggtggattt | gaaaatcacc | 300 |
| agtccgacag | tcgaggacac | ggccacctat | ttctgtgcca | gaggtctggg | tggtggtact | 360 |
| gtcatctggg | gcccaggcac | cctggtcacc | gtctccttag | ggcaacctaa | ggctccatca | 420 |
| gtcttcccac | tggcccctg | ctgcggggac | acacccagct | ccacggtgac | cctgggctgc | 480 |
| ctggtcaaag | ggtacctccc | ggagccagtg | accgtgacct | ggaactcggg | caccctcacc | 540 |
| aatggggtac | gcaccttccc | gtccgtccgg | cagtcctcag | gcctctactc | gctgagcagc | 600 |
| gtggtgagcg | tgacctcaag | cagccagccc | gtcacctgca | acgtggccca | cccagccacc | 660 |
| aacaccaaag | tggacaagac | cgttgcgccc | tcgacatgca | gcaagcccac | gtgcccaccc | 720 |
| cctgaactcc | tggggggacc | gtctgtcttc | atcttccccc | caaaacccaa | ggacaccctc | 780 |
| atgatctcac | gcacccccga | ggtcacatgc | gtggtggtgg | acgtgagcca | ggatgacccc | 840 |
| gaggtgcagt | tcacatggta | cataaacaac | gagcaggtgc | gcaccgcccg | gccgccgcta | 900 |
| cgggagcagc | agttcaacag | cacgatccgc | gtggtcagca | cctccccat | cgcgcaccag | 960 |
| gactggctga | ggggcaagga | gttcaagtgc | aaagtccaca | acaaggcact | cccggccccc | 1020 |
| atcgagaaaa | ccatctccaa | agccagaggg | cagcccctgg | agccgaaggt | ctacaccatg | 1080 |
| ggccctcccc | gggaggagct | gagcagcagg | tcggtcagcc | tgacctgcat | gatcaacggc | 1140 |
| ttctacccctt | ccgacatctc | ggtggagtgg | gagaagaacg | ggaaggcaga | ggacaactac | 1200 |
| aagaccacgc | cggccgtgct | ggacagcgac | ggctcctact | tcctctacag | caagctctca | 1260 |
| gtgcccacga | gtgagtggca | gcggggcgac | gtcttcacct | gctccgtgat | gcacgaggcc | 1320 |
| ttgcacaacc | actacacgca | gaagtccatc | tcccgctctc | cgggtaaatg | a | 1371 |

<210> SEQ ID NO 40
<211> LENGTH: 399
<212> TYPE: DNA
<213> ORGANISM: Oryctolagus cuniculus

<400> SEQUENCE: 40

```
atggagactg ggctgcgctg gcttctcctg gtcgctgtgc tcaaaggtgt ccagtgtcag    60
tcggtggagg agtccggggg tcgcctggtc acgcctggga caccccctgac actcacctgc   120 aaagcctctg gattctccct cagtgactct agagtgagct gggtccgcca ggctccaggg   180
aaggggctgg aatggatcgg aatcgttggc attggttgga atatatacca cgcgaactgg   240
gcgaaaggcc gattcaccat ctccaaaacg tcgtcgacca cggtggattt gaaaatcacc   300
agtccgacag tcgaggacac ggccacctat ttctgtgcca gaggtctggg tggtggtact   360
gtcatctggg gcccaggcac cctggtcacc gtctcctta                           399

<210> SEQ ID NO 41
<211> LENGTH: 720
<212> TYPE: DNA
<213> ORGANISM: Oryctolagus cuniculus

<400> SEQUENCE: 41
atggacacga gggcccccac tcagctgctg gggctcctgc tgctctggct cccaggtgcc    60
acatttgccc aagtgctgac ccagactcca gcctccgtgt ctgcagctgt gggaggcaca   120
gtcaccatca gttgccagtc cagtgagagt gtttataaga caactactt atcctggttt    180 cagcagaaac caggacagcc tcccaagctc ctgatctacg aagcatccaa actggcatct   240
ggggtctcaa cgcggttcaa aggcagtgga tctgggacac agttcactct caccatcagc   300
ggcgtgcagt gtgacgatgc tgccacatac tactgtctag cgaatttag ttgttatagt    360 ggtgattgtg gtactttcgg cggagggacc gcggtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga aacagtaaaa caccgcagaa ttctgcaga ttgtacctac    600 aacctcagca gcactctgac actgaccagc acacagtaca acagccacaa agagtacacc   660
tgcaaggtga cccagggcac gacctcagtc gtccagagct caataggg tgactgttag     720

<210> SEQ ID NO 42
<211> LENGTH: 405
<212> TYPE: DNA
<213> ORGANISM: Oryctolagus cuniculus

<400> SEQUENCE: 42
atggacacga gggcccccac tcagctgctg gggctcctgc tgctctggct cccaggtgcc    60
acatttgccc aagtgctgac ccagactcca gcctccgtgt ctgcagctgt gggaggcaca   120
gtcaccatca gttgccagtc cagtgagagt gtttataaga caactactt atcctggttt    180 cagcagaaac caggacagcc tcccaagctc ctgatctacg aagcatccaa actggcatct   240
ggggtctcaa cgcggttcaa aggcagtgga tctgggacac agttcactct caccatcagc   300
ggcgtgcagt gtgacgatgc tgccacatac tactgtctag cgaatttag ttgttatagt    360 ggtgattgtg gtactttcgg cggagggacc gcggtggtgg tcaaa                   405

<210> SEQ ID NO 43
<211> LENGTH: 458
<212> TYPE: PRT
<213> ORGANISM: Oryctolagus cuniculus

<400> SEQUENCE: 43

Met Glu Thr Gly Leu Arg Trp Leu Leu Leu Val Ala Val Leu Lys Gly
1               5                   10                  15
```

-continued

Val Gln Cys Gln Ser Leu Glu Glu Ser Gly Gly Arg Leu Val Thr Pro
                20                  25                  30
Gly Thr Pro Leu Thr Leu Thr Cys Thr Val Ser Gly Phe Ser Leu Ser
            35                  40                  45
Arg Asn Ala Ile Asn Trp Val Arg Gln Ala Pro Gly Lys Gly Leu Glu
50                  55                  60
Tyr Ile Gly Ile Ile Gly Ser Ser Gly Val Thr Tyr Tyr Ala Ser Trp
65                  70                  75                  80
Ala Lys Gly Arg Phe Thr Ile Ser Arg Thr Ser Thr Thr Val Asp Leu
                85                  90                  95
Lys Ile Thr Ser Pro Thr Thr Glu Asp Thr Ala Thr Tyr Phe Cys Ala
            100                 105                 110
Arg Asn Leu Tyr Thr Gly Gly Ser Asn Asp Asn Leu Trp Gly Pro Gly
        115                 120                 125
Thr Leu Val Thr Val Ser Ser Gly Gln Pro Lys Ala Pro Ser Val Phe
130                 135                 140
Pro Leu Ala Pro Cys Cys Gly Asp Thr Pro Ser Ser Thr Val Thr Leu
145                 150                 155                 160
Gly Cys Leu Val Lys Gly Tyr Leu Pro Glu Pro Val Thr Val Thr Trp
                165                 170                 175
Asn Ser Gly Thr Leu Thr Asn Gly Val Arg Thr Phe Pro Ser Val Arg
            180                 185                 190
Gln Ser Ser Gly Leu Tyr Ser Leu Ser Ser Val Val Ser Val Thr Ser
        195                 200                 205
Ser Ser Gln Pro Val Thr Cys Asn Val Ala His Pro Ala Thr Asn Thr
210                 215                 220
Lys Val Asp Lys Thr Val Ala Pro Ser Thr Cys Ser Lys Pro Thr Cys
225                 230                 235                 240
Pro Pro Pro Glu Leu Leu Gly Gly Pro Ser Val Phe Ile Phe Pro Pro
                245                 250                 255
Lys Pro Lys Asp Thr Leu Met Ile Ser Arg Thr Pro Glu Val Thr Cys
            260                 265                 270
Val Val Val Asp Val Ser Gln Asp Asp Pro Glu Val Gln Phe Thr Trp
        275                 280                 285
Tyr Ile Asn Asn Glu Gln Val Arg Thr Ala Arg Pro Pro Leu Arg Glu
290                 295                 300
Gln Gln Phe Asn Ser Thr Ile Arg Val Val Ser Thr Leu Pro Ile Ala
305                 310                 315                 320
His Gln Asp Trp Leu Arg Gly Lys Glu Phe Lys Cys Lys Val His Asn
                325                 330                 335
Lys Ala Leu Pro Ala Pro Ile Glu Lys Thr Ile Ser Lys Ala Arg Gly
            340                 345                 350
Gln Pro Leu Glu Pro Lys Val Tyr Thr Met Gly Pro Pro Arg Glu Glu
        355                 360                 365
Leu Ser Ser Arg Ser Val Ser Leu Thr Cys Met Ile Asn Gly Phe Tyr
        370                 375                 380
Pro Ser Asp Ile Ser Val Glu Trp Glu Lys Asn Gly Lys Ala Glu Asp
385                 390                 395                 400
Asn Tyr Lys Thr Thr Pro Ala Val Leu Asp Ser Asp Gly Ser Tyr Phe
                405                 410                 415
Leu Tyr Ser Lys Leu Ser Val Pro Thr Ser Glu Trp Gln Arg Gly Asp
            420                 425                 430

```
Val Phe Thr Cys Ser Val Met His Glu Ala Leu His Asn His Tyr Thr
            435                 440                 445

Gln Lys Ser Ile Ser Arg Ser Pro Gly Lys
    450                 455
```

<210> SEQ ID NO 44
<211> LENGTH: 135
<212> TYPE: PRT
<213> ORGANISM: Oryctolagus cuniculus

<400> SEQUENCE: 44

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Arg Asn Ala Ile Asn Trp Val Arg Gln Ala Pro Gly Lys Gly Leu Glu
    50                  55                  60

Tyr Ile Gly Ile Ile Gly Ser Ser Gly Val Thr Tyr Tyr Ala Ser Trp
65                  70                  75                  80

Ala Lys Gly Arg Phe Thr Ile Ser Arg Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Asn Leu Tyr Thr Gly Gly Ser Asn Asp Asn Leu Trp Gly Pro Gly
        115                 120                 125

Thr Leu Val Thr Val Ser Ser
    130                 135
```

<210> SEQ ID NO 45
<211> LENGTH: 237
<212> TYPE: PRT
<213> ORGANISM: Oryctolagus cuniculus

<400> SEQUENCE: 45

```
Met Asp Thr Arg Val Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Lys Ser Val Tyr Asn Asn Val Gln Leu Ser Trp Phe Gln Gln Lys Pro
    50                  55                  60

Gly Gln Pro Pro Lys Arg Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Val Ala Thr Tyr Tyr Cys
            100                 105                 110

Ala Gly Gly Tyr Ser Ser Ser Asp Asn Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160
```

```
Val Ala Asn Lys Tyr Phe Pro Asp Val Thr Val Thr Trp Glu Val Asp
            165                 170                 175

Gly Thr Thr Gln Thr Thr Gly Ile Glu Asn Ser Lys Thr Pro Gln Asn
        180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 46
<211> LENGTH: 133
<212> TYPE: PRT
<213> ORGANISM: Oryctolagus cuniculus

<400> SEQUENCE: 46

Met Asp Thr Arg Val Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Lys Ser Val Tyr Asn Asn Val Gln Leu Ser Trp Phe Gln Gln Lys Pro
    50                  55                  60

Gly Gln Pro Pro Lys Arg Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Val Ala Thr Tyr Tyr Cys
            100                 105                 110

Ala Gly Gly Tyr Ser Ser Ser Ser Asp Asn Ala Phe Gly Gly Gly Thr
        115                 120                 125

Glu Val Val Val Lys
    130

<210> SEQ ID NO 47
<211> LENGTH: 5
<212> TYPE: PRT
<213> ORGANISM: Oryctolagus cuniculus

<400> SEQUENCE: 47

Arg Asn Ala Ile Asn
1               5

<210> SEQ ID NO 48
<211> LENGTH: 16
<212> TYPE: PRT
<213> ORGANISM: Oryctolagus cuniculus

<400> SEQUENCE: 48

Ile Ile Gly Ser Ser Gly Val Thr Tyr Tyr Ala Ser Trp Ala Lys Gly
1               5                   10                  15

<210> SEQ ID NO 49
<211> LENGTH: 11
<212> TYPE: PRT
<213> ORGANISM: Oryctolagus cuniculus

<400> SEQUENCE: 49
```

Asn Leu Tyr Thr Gly Gly Ser Asn Asp Asn Leu
1               5                   10

<210> SEQ ID NO 50
<211> LENGTH: 13
<212> TYPE: PRT
<213> ORGANISM: Oryctolagus cuniculus

<400> SEQUENCE: 50

Gln Ala Ser Lys Ser Val Tyr Asn Asn Val Gln Leu Ser
1               5                   10

<210> SEQ ID NO 51
<211> LENGTH: 7
<212> TYPE: PRT
<213> ORGANISM: Oryctolagus cuniculus

<400> SEQUENCE: 51

Tyr Ala Ser Thr Leu Ala Ser
1               5

<210> SEQ ID NO 52
<211> LENGTH: 11
<212> TYPE: PRT
<213> ORGANISM: Oryctolagus cuniculus

<400> SEQUENCE: 52

Ala Gly Gly Tyr Ser Ser Ser Ser Asp Asn Ala
1               5                   10

<210> SEQ ID NO 53
<211> LENGTH: 1377
<212> TYPE: DNA
<213> ORGANISM: Oryctolagus cuniculus

<400> SEQUENCE: 53

| | | | | | |
|---|---|---|---|---|---|
| atggagactg | ggctgcgctg | gcttctcctg | gtcgctgtgc | tcaaaggtgt | ccagtgtcag | 60 |
| tcgttggagg | agtccggggg | tcgcctggtc | acgcctggga | cacccctgac | actcacctgc | 120 |
| accgtctctg | gattctccct | cagtcgcaat | gcaataaact | gggtccgcca | ggctccaggg | 180 |
| aaggggctgg | aatacatcgg | aatcattggt | agtagtggtg | tcacatacta | cgcgagctgg | 240 |
| gcaaaaggcc | gattcaccat | ctccagaacc | tcgaccacgg | tggatctgaa | aatcaccagt | 300 |
| ccgacaaccg | aggacacggc | cacctatttt | tgtgccagaa | atctttatac | tggtggtagt | 360 |
| aatgataact | tgtggggccc | aggcaccctg | gtcaccgtct | cctcagggca | acctaaggct | 420 |
| ccatcagtct | tcccactggc | ccctgctgc | ggggacacac | ccagctccac | ggtgaccctg | 480 |
| ggctgcctgg | tcaaagggta | cctcccggag | ccagtgaccg | tgacctggaa | ctcgggcacc | 540 |
| ctcaccaatg | ggtacgcac | cttcccgtcc | gtcggcagt | cctcaggcct | ctactcgctg | 600 |
| agcagcgtgt | tgagcgtgac | ctcaagcagc | cagcccgtca | cctgcaacgt | ggcccaccca | 660 |
| gccaccaaca | ccaaagtgga | caagaccgtt | gcgccctcga | catgcagcaa | gcccacgtgc | 720 |
| ccacccctg | aactcctggg | gggaccgtct | gtcttcatct | tccccccaaa | acccaaggac | 780 |
| accctcatga | tctcacgcac | ccccgaggtc | acatgcgtgg | tggtggacgt | gagccaggat | 840 |
| gaccccgagg | tgcagttcac | atggtacata | aacaacgagc | aggtgcgcac | cgcccggccg | 900 |
| ccgctacggg | agcagcagtt | caacagcacg | atccgcgtgg | tcagcaccct | ccccatcgcg | 960 |
| caccaggact | ggctgagggg | caaggagttc | aagtgcaaag | tccacaacaa | ggcactcccg | 1020 |

```
gcccccatcg agaaaaccat ctccaaagcc agagggcagc ccctggagcc gaaggtctac    1080
accatgggcc ctccccggga ggagctgagc agcaggtcgg tcagcctgac ctgcatgatc    1140
aacggcttct acccttccga catctcggtg gagtgggaga agaacgggaa ggcagaggac    1200
aactacaaga ccacgccggc cgtgctggac agcgacggct cctacttcct ctacagcaag    1260
ctctcagtgc ccacgagtga gtggcagcgg ggcgacgtct tcacctgctc cgtgatgcac    1320
gaggccttgc acaaccacta cacgcagaag tccatctccc gctctccggg taaatga       1377

<210> SEQ ID NO 54
<211> LENGTH: 405
<212> TYPE: DNA
<213> ORGANISM: Oryctolagus cuniculus

<400> SEQUENCE: 54
atggagactg ggctgcgctg gcttctcctg gtcgctgtgc tcaaaggtgt ccagtgtcag     60
tcgttggagg agtccggggg tcgcctggtc acgcctggga caccctgac actcacctgc    120 accgtctctg gattctccct cagtcgcaat gcaataaact gggtccgcca ggctccaggg    180
aaggggctgg aatacatcgg aatcattggt agtagtggtg tcacatacta cgcgagctgg    240
gcaaaaggcc gattcaccat ctccagaacc tcgaccacgg tggatctgaa aatcaccagt    300
ccgacaaccg aggacacggc cacctatttt tgtgccagaa atctttatac tggtggtagt    360
aatgataact tgtggggccc aggcaccctg gtcaccgtct cctca                    405

<210> SEQ ID NO 55
<211> LENGTH: 1371
<212> TYPE: DNA
<213> ORGANISM: Oryctolagus cuniculus

<400> SEQUENCE: 55
atggagactg ggctgcgctg gcttctcctg gtcgctgtgc tcaaaggtgt ccagtgtcag     60
tcggtggagg agtccggggg tcgcctggtc acgcctggga caccctgac actcacctgc    120 aaagcctctg gattctccct cagtgactct agagtgagct gggtccgcca ggctccaggg    180
aaggggctgg aatggatcgg aatcgttggc attggttgga atatataccca cgcgaactgg    240 gcgaaaggcc gattcaccat ctccaaaacg tcgtcgacca cggtggattt gaaaatcacc    300
agtccgacag tcgaggacac ggccacctat ttctgtgcca gaggtctggg tggtggtact    360
gtcatctggg gcccaggcac cctggtcacc gtctccttag ggcaacctaa ggctccatca    420
gtcttcccac tggccccctg ctgcggggac acacccagct ccacggtgac cctgggctgc    480
ctggtcaaag ggtacctccc ggagccagtg accgtgacct ggaactcggg caccctcacc    540
aatggggtac gcaccttccc gtccgtccgg cagtcctcag gcctctactc gctgagcagc    600
gtggtgagcg tgacctcaag cagccagccc gtcacctgca acgtggccca cccagccacc    660
aacaccaaag tggacaagac cgttgcgccc tcgacatgca gcaagcccac gtgcccaccc    720
cctgaactcc tgggggggacc gtctgtcttc atcttccccc caaaacccaa ggacaccctc    780
atgatctcac gcaccccccga ggtcacatgc gtggtggtgg acgtgagcca ggatgacccc    840
gaggtgcagt tcatggtgta cataaacaac gagcaggtgc gcaccgcccg gccgccgcta    900
cgggagcagc agttcaacag cacgatccgc gtggtcagca ccctccccat cgcgcaccag    960
gactggctga ggggcaagga gttcaagtgc aaagtcccaca acaaggcact cccggccccc   1020
atcgagaaaa ccatctccaa agccagaggg cagcccctgg agccgaaggt ctacaccatg    1080
ggccctcccc gggaggagct gagcagcagg tcggtcagcc tgacctgcat gatcaacggc    1140
```

```
ttctacccTT ccgacatctc ggtggagtgg gagaagaacg ggaaggcaga ggacaactac    1200
aagaccacgc cggccgtgct ggacagcgac ggctcctact tcctctacag caagctctca    1260
gtgcccacga gtgagtggca gcggggcgac gtcttcacct gctccgtgat gcacgaggcc    1320
ttgcacaacc actacacgca gaagtccatc tcccgctctc cgggtaaatg a             1371

<210> SEQ ID NO 56
<211> LENGTH: 399
<212> TYPE: DNA
<213> ORGANISM: Oryctolagus cuniculus

<400> SEQUENCE: 56
atggagactg ggctgcgctg gcttctcctg gtcgctgtgc tcaaaggtgt ccagtgtcag      60
tcggtggagg agtccggggg tcgcctggtc acgcctggga cacccctgac actcacctgc    120
aaagcctctg gattctcccT cagtgactct agagtgagct gggtccgcca ggctccaggg    180
aaggggctgg aatggatcgg aatcgttggc attggttgga atatatacca cgcgaactgg    240
gcgaaaggcc gattcaccat ctccaaaacg tcgtcgacca cggtggattt gaaaatcacc    300
agtccgacag tcgaggacac ggccacctat ttctgtgcca gaggtctggg tggtggtact    360
gtcatctggg gcccaggcac cctggtcacc gtctcctta                            399

<210> SEQ ID NO 57
<211> LENGTH: 13
<212> TYPE: PRT
<213> ORGANISM: Artificial Sequence
<220> FEATURE:
<223> OTHER INFORMATION: PADRE Epitope

<400> SEQUENCE: 57

Ala Lys Phe Val Ala Ala Trp Thr Leu Lys Ala Ala Ala
1               5                   10

<210> SEQ ID NO 58
<211> LENGTH: 1415
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(18)
<223> OTHER INFORMATION: vector sequence
<220> FEATURE:
<221> NAME/KEY: source
<222> LOCATION: (19)..(1389)
<223> OTHER INFORMATION: AMF-3a-118 heavy chain-encoding DNA
<220> FEATURE:
<221> NAME/KEY: source
<222> LOCATION: (1390)..(1415)
<223> OTHER INFORMATION: vector sequence

<400> SEQUENCE: 58
aagcttgtac ccttcaccat ggagactggg ctgcgctggc ttctcctggt cgctgtgctc      60
aaaggtgtcc agtgtcagtc ggtggaggag tccgggggtc gcctggtcac gcctgggaca    120
cccctgacac tcacctgcaa agcctctgga ttctccctca gtgactctag agtgagctgg    180
gtccgccagg ctccagggaa ggggctggaa tggatcggaa tcgttggcat tggttggaat    240
atataccacg cgaactgggc gaaaggccga ttcaccatct ccaaaacgtc gtcgaccacg    300
gtggatttga aaatcaccag tccgacagtc gaggacacgg ccacctattt ctgtgccaga    360
ggtctgggtg gtggtactgt catctggggc ccaggcaccc tggtcaccgt ctccttaggg    420
```

```
caacctaagg ctccatcagt cttcccactg gcccsctgct gcggggacac acccagctcc    480
acggtgaccc tgggctgcct ggtcaaaggg tacctcccgg agccagtgac cgtgacctgg    540
aactcgggca ccctcaccaa tggggtacgc accttcccgt ccgtccggca gtcctcaggc    600
ctctactcgc tgagcagcgt ggtgagcgtg acctcaagca gccagccgt cacctgcaac     660 gtggcccacc cagccaccaa caccaaagtg gacaagaccg ttgcgccctc gacatgcagc    720
aagcccacgt gcccaccccc tgaactcctg gggggaccgt ctgtcttcat cttccccca    780 aaacccaagg acaccctcat gatctcacgc accccgagg tcacatgcgt ggtggtggac    840
gtgagccagg atgaccccga ggtgcagttc acatggtaca taaacaacga gcaggtgcgc    900
accgcccggc cgccgctacg ggagcagcag ttcaacagca cgatccgcgt ggtcagcacc    960
ctccccatcg cgcaccagga ctggctgagg ggcaaggagt caagtgcaa agtccacaac   1020 aaggcactcc cggcccccat cgagaaaacc atctccaaag ccagagggca gccctggag    1080 ccgaaggtct acaccatggg ccctcccgg gaggagctga gcagcaggtc ggtcagcctg    1140
acctgcatga tcaacggctt ctacccttcc gacatctcgg tggagtggga agaacggg     1200 aaggcagagg acaactacaa gaccacgccg ccgtgctgg acagcgacgg ctcctacttc    1260
ctctacagca agctctcagt gcccacgagt gagtggcagc ggggcgacgt cttcacctgc    1320
tccgtgatgc acgaggcctt gcacaaccac tacacgcaga agtccatctc ccgctctccg    1380
ggtaaatgag cgctgtgccg gcgagctgcg gccgc                               1415

<210> SEQ ID NO 59
<211> LENGTH: 753
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(18)
<223> OTHER INFORMATION: vector sequence
<220> FEATURE:
<221> NAME/KEY: source
<222> LOCATION: (19)..(738)
<223> OTHER INFORMATION: AMF 3a-118 light chain-encoding DNA
<220> FEATURE:
<221> NAME/KEY: source
<222> LOCATION: (739)..(753)
<223> OTHER INFORMATION: vector sequence

<400> SEQUENCE: 59
aagcttgtac ccttcaccat ggacacgagg gcccccactc agctgctggg gctcctgctg     60
ctctggctcc caggtgccac atttgcccaa gtgctgaccc agactccagc ctccgtgtct    120
gcagctgtgg gaggcacagt caccatcagt tgccagtcca gtgagagtgt ttataagaac    180
aactacttat cctggtttca gcagaaacca ggacagcctc caagctcct gatctacgaa     240 gcatccaaac tggcatctgg ggtctcaacg cggttcaaag cagtggatc tgggacacag    300 ttcactctca ccatcagcgg cgtgcagtgt gacgatgctg ccacatacta ctgtctaggc    360
gaatttagtt gttatagtgg tgattgtggt actttcggcg agggaccgc ggtggtggtc    420 aaaggtgatc cagttgcacc tactgtcctc atcttcccac cagctgctga tcaggtggca    480
actggaacag tcaccatcgt gtgtgtggcg aataaatact ttcccgatgt caccgtcacc    540
tgggaggtgg atggcaccac ccaaacaact ggcatcgaga cagtaaaaac accgcagaat    600
tctgcagatt gtacctacaa cctcagcagc actctgacac tgaccagcac acagtacaac    660
```
agccacaaag agtacacctg caaggtgacc cagggcacga cctcagtcgt ccagagcttc    720 aatagggtg actgttagag tgagagcggc cgc    753

<210> SEQ ID NO 60
<211> LENGTH: 1421
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(18)
<223> OTHER INFORMATION: vector sequence
<220> FEATURE:
<221> NAME/KEY: source
<222> LOCATION: (19)..(1395)
<223> OTHER INFORMATION: AMF 3d-19 heavy chain-encoding DNA
<220> FEATURE:
<221> NAME/KEY: source
<222> LOCATION: (1396)..(1421)
<223> OTHER INFORMATION: vector sequence

<400> SEQUENCE: 60
aagcttgtac ccttcaccat ggagactggg ctgcgctggc ttctcctggt cgctgtgctc    60
aaaggtgtcc agtgtcagtc gttggaggag tccgggggtc gcctggtcac gcctgggaca    120
cccctgacac tcacctgcac cgtctctgga ttctccctca gtcgcaatgc aataaactgg    180
gtccgccagg ctccagggaa ggggctggaa tacatcggaa tcattggtag tagtggtgtc    240
acatactacg cgagctgggc aaaaggccga ttcaccatct ccagaacctc gaccacggtg    300
gatctgaaaa tcaccagtcc gacaaccgag gacacggcca cctattttg tgccagaaat    360 ctttatactg gtggtagtaa tgataacttg tggggcccag gcaccctggt caccgtctcc    420
tcagggcaac ctaaggctcc atcagtcttc ccactggccc cctgctgcgg ggacacaccc    480
agctccacgg tgaccctggg ctgcctggtc aaagggtacc tcccggagcc agtgaccgtg    540
acctggaact cgggcaccct caccaatggg gtacgcacct tcccgtccgt ccggcagtcc    600
tcaggcctct actcgctgag cagcgtggtg agcgtgacct caagcagcca gcccgtcacc    660
tgcaacgtgg cccacccagc caccaacacc aaagtggaca gaccgttgc gccctcgaca    720 tgcagcaagc ccacgtgccc acccctgaa ctcctggggg gaccgtctgt cttcatcttc    780 ccccaaaac ccaaggacac cctcatgatc tcacgcaccc ccgaggtcac atgcgtggtg    840
gtggacgtga gccaggatga ccccgaggtg cagttcacat ggtacataaa caacgagcag    900
gtgcgcaccg cccggccgcc gctacgggag cagcagttca acagcacgat ccgcgtggtc    960
agcaccctcc ccatcgcgca ccaggactgg ctgaggggca aggagttcaa gtgcaaagtc    1020
cacaacaagg cactcccggc cccatcgag aaaaccatct ccaaagccag agggcagccc    1080
ctggagccga aggtctacac catgggccct cccgggagg agctgagcag caggtcggtc    1140
agcctgacct gcatgatcaa cggcttctac ccttccgaca tctcggtgga gtgggagaag    1200

```
aacgggaagg cagaggacaa ctacaagacc acgccggccg tgctggacag cgacggctcc    1260
tacttcctct acagcaagct ctcagtgccc acgagtgagt ggcagcgggg cgacgtcttc    1320
acctgctccg tgatgcacga ggccttgcac aaccactaca cgcagaagtc catctcccgc    1380
tctccgggta aatgagcgct gtgccggcga gctgcggccg c                         1421
```

<210> SEQ ID NO 61
<211> LENGTH: 1415
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(18)
<223> OTHER INFORMATION: vector sequence
<220> FEATURE:
<221> NAME/KEY: source
<222> LOCATION: (19)..(1389)
<223> OTHER INFORMATION: AMF 3d-19 light chain-encoding DNA
<220> FEATURE:
<221> NAME/KEY: source
<222> LOCATION: (1390)..(1415)
<223> OTHER INFORMATION: vector sequence

<400> SEQUENCE: 61

```
aagcttgtac ccttcaccat ggagactggg ctgcgctggc ttctcctggt cgctgtgctc      60
aaaggtgtcc agtgtcagtc ggtggaggag tccggggggtc gcctggtcac gcctgggaca    120
cccctgacac tcacctgcaa agcctctgga ttctccctca gtgactctag agtgagctgg    180
gtccgccagg ctccagggaa ggggctggaa tggatcggaa tcgttggcat tggttggaat    240
atataccacg cgaactgggc gaaaggccga ttcaccatct ccaaaacgtc gtcgaccacg    300
gtggatttga aaatcaccag tccgacagtc gaggacacgg ccacctatttc tgtgccaga    360 ggtctgggtg gtggtactgt catctggggc ccaggcaccc tggtcaccgt ctccttaggg    420
caacctaagg ctccatcagt cttcccactg gccccctgct gcggggacac acccagctcc    480
acggtgaccc tgggctgcct ggtcaaaggg tacctcccgg agccagtgac cgtgacctgg    540
aactcgggca ccctcaccaa tggggtacgc accttcccgt ccgtcggca gtcctcaggc    600 ctctactcgc tgagcagcgt ggtgagcgtg acctcaagca gccagcccgt cacctgcaac    660
gtggcccacc cagccaccaa caccaaagtg gacaagaccg ttgcgccctc gacatgcagc    720
aagcccacgt gcccaccccc tgaactcctg ggggaccgt ctgtcttcat cttccccca    780 aaacccaagg acaccctcat gatctcacgc accccgagg tcacatgcgt ggtggtggac    840
gtgagccagg atgaccccga ggtgcagttc acatggtaca taaacaacga gcaggtgcgc    900 accgccggc cgccgctacg ggagcagcag ttcaacagca cgatccgcgt ggtcagcacc    960
ctccccatcg cgcaccagga ctggctgagg ggcaaggagt tcaagtgcaa agtccacaac    1020
aaggcactcc cggccccccat cgagaaaacc atctccaaag ccagagggca gccctggag    1080 ccgaaggtct acaccatggg ccctcccgg gaggagctga gcagcaggtc ggtcagcctg    1140
acctgcatga tcaacggctt ctaccttcc gacatctcgg tggagtggga agaacgggg    1200 aaggcagagg acaactacaa gaccacgccg ccgtgctgg acagcgacgg ctcctacttc    1260
ctctacagca gctctcagt gcccacgagt gagtggcagc ggggcgacgt cttcacctgc    1320
tccgtgatgc acgaggcctt gcacaaccac tacacgcaga agtccatctc ccgctctccg    1380
ggtaaatgag cgctgtgccg gcgagctgcg gccgc                                 1415
```

The invention claimed is:

1. An antibody or fragment thereof that binds selectively to a misfolded form of human Fas receptor (FasR), wherein the antibody or fragment thereof binds to an epitope comprising at least 5 contiguous residues of LHHDGQFCH (SEQ ID No. 2) of the misfolded human FasR, the antibody comprising a heavy chain and a light chain, each chain having a constant region and a variable region, each variable region comprising framework regions and complementarity determining regions (CDRs), wherein the CDRs comprise the amino acid sequence set forth below:

For the heavy chain:

| | | |
|---|---|---|
| CDR1 | (SEQ ID No. 33) | |
| CDR2 | (SEQ ID No. 34) | |
| CDR3 | (SEQ ID No. 35) | |

For the light chain:

| | | |
|---|---|---|
| CDR1 | (SEQ ID No. 36) | |
| CDR2 | (SEQ ID No. 37) | |
| CDR3 | (SEQ ID No. 38). | |

2. An antibody or binding fragment thereof according to claim 1, wherein the light chain variable region comprises SEQ ID NO. 32 and/or wherein the heavy chain variable region comprises SEQ ID NO. 30.

3. An antibody according to claim 2, wherein the light chain comprises SEQ ID No. 31 and/or wherein the heavy chain comprises SEQ ID No. 29.

4. A diagnostic kit comprising the antibody or binding fragment according to claim 1 or an immunoconjugate thereof, and instructions for the use thereof to detect cells presenting misfolded human FasR.

5. An immunoconjugate comprising the antibody or binding fragment according to claim 1, conjugated with a toxin or a detectable label.

6. An immunoconjugate comprising the antibody or binding fragment defined by claim 2 conjugated to a toxin or a detectable label.

7. An immunoconjugate comprising the antibody defined by claim 3 of conjugated to a toxin or a detectable label.

8. A pharmaceutical composition comprising the antibody or binding fragment according to claim 1, or an immunoconjugate thereof, and a pharmaceutically acceptable carrier.

9. A pharmaceutical composition comprising the antibody or binding fragment of claim 2, or an immunoconjugate thereof, and a pharmaceutically acceptable carrier.

10. A pharmaceutical composition comprising the antibody of claim 3, or an immunoconjugate thereof, and a pharmaceutically acceptable carrier.

11. A method for detecting, in a biological sample, cells that present misfolded FasR, the method comprising incubating the sample with the antibody or binding fragment according to claim 1 or an immunoconjugate thereof, and detecting formation of an antibody-bound complex.

12. A method for detecting, in a biological sample, cells that present misfolded FasR, the method comprising incubating the sample with the antibody or binding fragment according to claim 2 or an immunoconjugate thereof, and detecting formation of an antibody-bound complex.

13. A method for detecting, in a biological sample, cells that present misfolded FasR, the method comprising incubating the sample with the antibody according to claim 3 or an immunoconjugate thereof, and detecting formation of an antibody-bound complex.

* * * * *

UNITED STATES PATENT AND TRADEMARK OFFICE
CERTIFICATE OF CORRECTION

PATENT NO. : 10,053,510 B2
APPLICATION NO. : 14/893847
DATED : August 21, 2018
INVENTOR(S) : Marni Diane Uger, Veronica Ciolfi and Neil R. Cashman Page 1 of 1

It is certified that error appears in the above-identified patent and that said Letters Patent is hereby corrected as shown below:

In the Specification

Column 29, Line 54 should read as follows:
36 Ab 3a-118 CDR1 light QSSESVYKNNYLS Column 45, Line 43 should read as follows:
<211> LENGHT: 13

Column 45, Lines 47-48 should read as follows:
Gln Ser Ser Glu Ser Val Tyr Lys Asn Asn Tyr Leu Ser
1                5                      10

Signed and Sealed this
Sixteenth Day of July, 2019

Andrei Iancu
*Director of the United States Patent and Trademark Office*